(12) United States Patent
McDonagh et al.

(10) Patent No.: US 9,247,766 B2
(45) Date of Patent: Feb. 2, 2016

(54) ANGIOGENIN-ENRICHED MILK FRACTIONS

(75) Inventors: Matthew McDonagh, Williamstown (AU); Benjamin Cocks, Viewbank (AU); Angus Tester, Moonee Ponds (AU); Peter Hobman, Melbourne (AU); Andrew Brown, Cobram (AU)

(73) Assignees: Murray Goulburn Co-Operative Co., Limited, Southbank (AU); Agriculture Victoria Services Pty Ltd., Attwood (AU)

( * ) Notice: Subject to any disclaimer, the term of this patent is extended or adjusted under 35 U.S.C. 154(b) by 790 days.

(21) Appl. No.: 12/992,530

(22) PCT Filed: May 14, 2009

(86) PCT No.: PCT/AU2009/000604
§ 371 (c)(1),
(2), (4) Date: Feb. 7, 2011

(87) PCT Pub. No.: WO2009/137881
PCT Pub. Date: Nov. 19, 2009

(65) Prior Publication Data
US 2011/0123514 A1    May 26, 2011

(30) Foreign Application Priority Data

| May 14, 2008 | (AU) | 2008902366 |
| May 14, 2008 | (AU) | 2008902369 |
| May 14, 2008 | (AU) | 2008902373 |
| May 14, 2008 | (AU) | 2008902375 |

(51) Int. Cl.
A61K 38/46    (2006.01)
C12N 9/22     (2006.01)
A23L 1/305    (2006.01)
A23J 1/20     (2006.01)
(Continued)

(52) U.S. Cl.
CPC .............. *A23L 1/3053* (2013.01); *A23J 1/20* (2013.01); *A23L 1/3056* (2013.01); *C07K 14/515* (2013.01); *A61K 38/00* (2013.01)

(58) Field of Classification Search
None
See application file for complete search history.

(56) References Cited

U.S. PATENT DOCUMENTS 3,149,060 A * 9/1964 Reuven et al. ............ 204/549
5,171,845 A   12/1992 Spik et al.
(Continued)

FOREIGN PATENT DOCUMENTS

JP    2004331566 A    11/2004
RU    2109748 C1       4/1998
(Continued)

OTHER PUBLICATIONS

Yoon et al. "High Level Expression of Soluble Angiogenin in *Eschericia coli*" Biochemistry and Molecular Biology International, vol. 47, No. 2 Feb. 1999, pp. 267-273.*
(Continued)

*Primary Examiner* — Lauren K Van Buren
(74) *Attorney, Agent, or Firm* — Clark & Elbing LLP

(57) ABSTRACT

The invention provides methods for enriching a milk extract for angiogenin, such methods involving separation by size, charge or immunoaffinity. The invention also provides the angiogenin enriched extract produced by the methods and provides them in pharmaceutical and neutraceutical compositions and foods for treating a variety of diseases or disorders that can be treated by angiogenin.

17 Claims, 8 Drawing Sheets

1  2  3

← IgG heavy chain (50kDa)

← IgG light chain (25kDa)

← Angiogenin

(51) Int. Cl.
*C07K 14/515* (2006.01)
*A61K 38/00* (2006.01)

(56) References Cited

U.S. PATENT DOCUMENTS

| | | | |
|---|---|---|---|
| 5,352,468 A * | 10/1994 | Schroder | 426/330.2 |
| 5,698,185 A | 12/1997 | Itagaki et al. | |
| 6,010,698 A * | 1/2000 | Kussendrager et al. | 424/94.1 |
| 6,268,487 B1 * | 7/2001 | Kutzko et al. | 530/414 |
| 2004/0117863 A1 * | 6/2004 | Edge et al. | 800/7 |
| 2005/0247563 A1 * | 11/2005 | Shuber et al. | 204/450 |
| 2005/0260672 A1 * | 11/2005 | Couto et al. | 435/6 |
| 2006/0280748 A1 * | 12/2006 | Buckheit, Jr. | 424/155.1 |
| 2007/0192878 A1 | 8/2007 | Perreault | |
| 2008/0254018 A1 | 10/2008 | Naidu | |
| 2008/0255340 A1 | 10/2008 | Naidu | |

FOREIGN PATENT DOCUMENTS

| | | |
|---|---|---|
| RU | 2110066 C1 | 4/1998 |
| WO | WO 2004/094207 | 11/2004 |
| WO | WO 2008/055310 | 5/2008 |

OTHER PUBLICATIONS

Yoon et al. "High Level Expression of Soluble Angiogenin in *Eschericia coli*" Biochemistry and Molecular Biology, vol. 47, No. 2, Feb. 1999, pp. 267-273.*

Janeway et al. Immunobiology, 6th Edition, 2005 by Garland Science Publishing, p. 689.*

Fedorova et al., "Preparing a Biologically Active Protein Concentrate Enriched with Pancreatic Ribonuclease A, Angiogenin and Lysozyme from Dairy Ultrafiltrate," RU 2204262C2, Derwent Abstract Accession No. 2003-552782 (2003).

International Search Report, PCT/AU2009/000604, completed on Jun. 2, 2009 and mailed on Jun. 9, 2009.

International Preliminary Report on Patentability, PCT/AU2009/000604, completed Jul. 30, 2010.

Extended European Search Report dated May 24, 2011, for European Patent Application No. 09745303.9, filed on May 14, 2009 (9 pages).

* cited by examiner

ANGIOGENIN-ENRICHED MILK FRACTIONS

CROSS REFERENCE TO RELATED APPLICATIONS

This application is the U.S. National Stage of International Application No. PCT/AU2009/000604, filed May 14, 2009, which claims the benefit of Australian Patent Application Nos. 2008902373, 2008902366, 2008902369, and 2008902375, all filed May 14, 2008, and each of which is hereby incorporated by reference.

The present invention relates to methods for obtaining a product enriched for angiogenin from a milk sample, and to the use of such a product as a food additive, nutraceutical, pharmaceutical or veterinary product, or for the preparation of a therapeutic composition.

BACKGROUND

Angiogenin is a 14 kDa non-glycosylated polypeptide which is produced by several growing cell types including vascular endothelial cells, aortic smooth muscle cells, fibroblasts, and some tumours such as colon carcinomas, ovarian carcinomas, and breast cancers. Angiogenin has been isolated from a number of sources including normal human plasma, bovine plasma, bovine milk, and mouse, rabbit and pig sera. In each of these sources angiogenin is present at low levels (less than 12 mg/L in bovine milk and less than 150 µL/L in human plasma).

As well as a potent stimulator of angiogenesis, angiogenin has been shown to possess a number of other activities. These include the ability to remove skin defects such as pigmented spots, modulation of immune responses, protection of polymorphonuclear leukocytes from spontaneous degradation, and microbicidal activity against systemic bacterial and fungal pathogens. Based on the known physiological functions of the protein, various angiogenin applications in medicine, dietary foodstuff supplements and cosmetics can be predicted.

The use of angiogenin in such applications requires an efficient method for the preparation of the protein on a commercial scale from an appropriate source. It is an aim of a preferred embodiment of the present invention to provide such a method.

SUMMARY OF THE INVENTION

Whilst bovine milk is a highly abundant commodity, its use as a source of angiogenin is not favoured as angiogenin is only present in bovine milk at a low level and certain proteins such as immunoglobulin, lactoferrin and lactoperoxidase present in milk mask angiogenin, hindering its purification. The inventors have found several methods for enriching a milk fraction for angiogenin, as described in the first to fifth aspects below and in their application published as WO2008/055310, each of which methods is able to produce a product enriched for angiogenin from milk.

A first aspect provides a method of obtaining a product enriched for angiogenin from a milk sample, said method comprising:

(a) contacting the milk sample with a capture agent which interacts with angiogenin, such that angiogenin present in the milk sample interacts with the capture agent to form an angiogenin-capture agent complex;

(b) separating the complex from the milk sample;

(c) releasing angiogenin from the capture agent in the complex; and (d) collecting the angiogenin from step (c) thereby obtaining a product enriched for angiogenin.

In one embodiment the capture agent is immobilised to a support.

In a further embodiment the capture agent is an antibody.

A second aspect provides a method of obtaining a product enriched for angiogenin from a milk sample, said method comprising:

(a) adding the milk sample to a support onto which is immobilised an antibody which interacts with angiogenin, wherein the angiogenin present in the milk sample interacts with the antibody on the support to form an angiogenin-antibody complex;

(b) washing constituents present in the milk sample which do not interact with the antibody from the support to separate the complex from the milk sample;

(c) releasing the angiogenin from the antibody in the complex; and (d) collecting the angiogenin from step (c) thereby obtaining a product enriched for angiogenin.

In one embodiment of the first or second aspect the method involves immunoaffinity chromatography.

A third aspect provides a method of obtaining a product enriched for angiogenin from a milk sample, said method comprising:

(a) adding a liquid phase milk sample to a second phase, said second phase enabling constituents of the milk sample to be separated based on the size of the constituents; and (b) collecting angiogenin which is separated from other constituents of the milk sample, thereby obtaining a product enriched for angiogenin, wherein prior to step (a), the milk sample is not subject to rennetting or acid precipitation, or alternatively the milk sample is not whey or a whey fraction.

In one embodiment of the third aspect the second phase is a semi-permeable phase.

In further embodiments of the third aspect the semi-permeable phase allows constituents less than 20 kDa in size, or even less than 50 kDa in size, to pass through the semi-permeable phase as a permeate. In a preferred embodiment the semi-permeable phase allows constituents less than 30 kDa in size to pass through the semi-permeable phase as a permeate. In such embodiments angiogenin passes through the semi-permeable phase as a permeate.

In a still further embodiment of the third aspect the semi-permeable phase allows constituents less than 10 kDa in size to pass through the semi-permeable phase as a permeate. In such an embodiment angiogenin is retained by the semi-permeable phase as a retentate.

In an even further embodiment of the third aspect the milk sample is forced through the semi-permeable phase.

In one embodiment of the third aspect the milk sample is forced through the semi-permeable phase by means of force applied by a syringe, compressed gas, a pump, centrifugal force, or a combination thereof.

In one embodiment of the third aspect, the second phase is a semi-permeable membrane.

In a further embodiment of the third aspect, the method involves ultrafiltration.

A fourth aspect provides a method of obtaining a product enriched for angiogenin from a milk sample, said method comprising:

(a) adding a liquid phase milk sample to a second phase, said second phase enabling constituents of the milk sample to be separated into fractions based on the size of the constituents;

(b) identifying those fractions containing angiogenin and collecting said fractions to obtain a product enriched for angiogenin.

In one embodiment of the fourth aspect the method involves size exclusion chromatography.

In a further embodiment of the fourth aspect, the second phase is a size exclusion resin.

In one embodiment of the fourth aspect, the resin separates proteins with a molecular weight of between about 10 and 20 kDa.

A fifth aspect provides a method of obtaining a product enriched for angiogenin from a milk sample, said method comprising:

(a) applying an electric field to a flowing aqueous milk sample in a direction transverse to the milk flow;

(b) recovering fractions of the milk flow to which the electric field has been applied; and (c) identifying those fractions enriched for angiogenin and collecting said fractions, thereby obtaining a product enriched for angiogenin.

In one embodiment of the fifth aspect the method involves free flow electrophoresis. The free flow electrophoresis may be selected from the group consisting of isoelectric focussing, zone electrophoresis, isotachophoresis, field step electrophoresis, and field flow fractionation. Furthermore, the free flow electrophoresis may be continuous free flow electrophoresis or interval free flow electrophoresis.

In a further embodiment, the method is conducted under denaturing conditions.

In a further embodiment of the fifth aspect, the flow of aqueous milk is conducted in a buffer medium which provides a pH gradient. In one embodiment, the gradient is in the pH range 8 to 11.

In a further embodiment of any one of the first to fifth aspects, the product enriched for angiogenin is subject to one or more further angiogenin enrichment steps. The one or more further angiogenin enrichment steps may be selected from the group consisting of cation exchange chromatography, electrophoresis including free flow electrophoresis, size exclusion chromatography and ultrafiltration. This is particularly if purity of the angiogenin fraction is an issue, e.g. for pharmaceutical use of the angiogenin. However it is envisaged that the method of the first and second aspects is able to provide an angiogenin enriched product of relatively high purity, depending on the specificity of the capture agent. Higher purity is envisaged when the capture is an antibody specific for angiogenin.

A sixth aspect provides a product enriched for angiogenin, when prepared by a method according to any one of the first to fifth aspects.

A seventh aspect provides the use of a product enriched for angiogenin according to the sixth aspect of the invention, in the preparation of a food substance, nutraceutical, pharmaceutical or veterinary product.

An eighth aspect provides a food substance, nutraceutical, pharmaceutical or veterinary product comprising a product enriched for angiogenin according to the sixth aspect.

In an embodiment of the seventh or eighth aspects, the food substance is a sport nutrition or food supplement, particularly a food supplement for infants, athletes, particularly elite athletes, the elderly or the infirm.

A ninth aspect provides a pharmaceutical composition or veterinary composition comprising a product enriched for angiogenin according to the sixth aspect.

A tenth aspect provides use of a product enriched for angiogenin according to the sixth aspect, in the preparation of a medicament for treating and/or preventing diseases caused by viruses, bacteria, or fungi and their toxins, or diseases where the stimulation of angiogenesis is required.

An eleventh aspect provides the use of a product enriched for angiogenin according to the sixth aspect, as an ingredient for a nutraceutical, pharmaceutical or veterinary product which can target pathogens which cause infections of mucosal surfaces.

A twelfth aspect provides a method of targeting pathogens which cause infections of mucosal surfaces, comprising the step of administering an effective amount of a nutraceutical, pharmaceutical or veterinary product according to the eighth aspect of the invention, or a composition according to the ninth aspect, to a subject.

In one embodiment of the eleventh or twelfth aspect of the invention, the mucosal surfaces may include those of the nose, eyes, ears, lungs, breast and vagina.

A thirteenth aspect provides a method of treating and/or preventing diseases caused by viruses, bacteria, or fungi and their toxins, or diseases where the stimulation of angiogenesis is required, comprising the step of administering an effective, amount of a nutraceutical, pharmaceutical or veterinary product according to an eighth aspect, or a composition according to the ninth aspect, to a subject.

DETAILED DESCRIPTION

Figure 1:
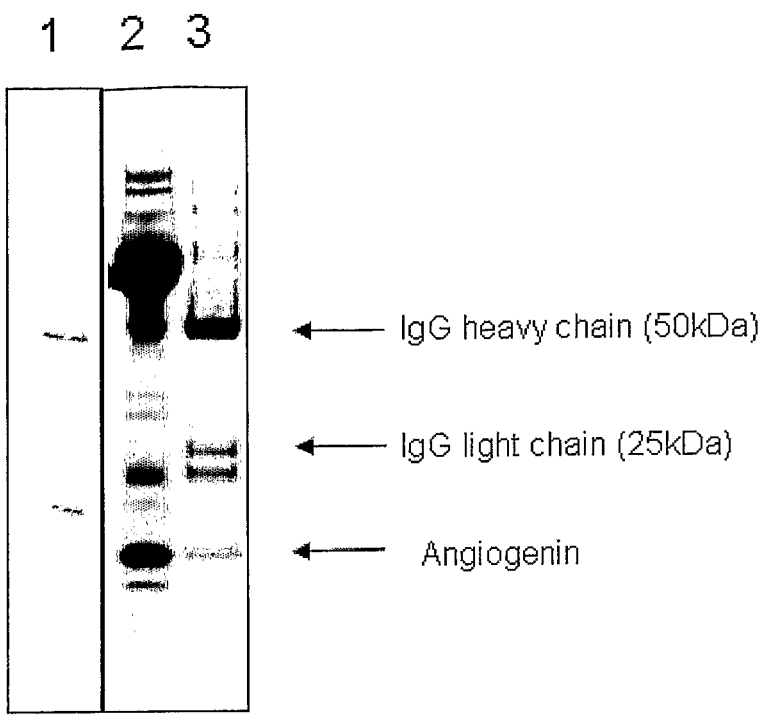
FIG. 1 shows a one dimensional SDS polyacrylamide gel stained with Sypro Ruby (Molecular Probes) and imaged using a 5 second exposure on a ProXpress (Perkin Elmer) imaging system. Lanes 1, 2 and 3 are 1) the molecular weight standard, 2) the milk derived fraction, and 3) the eluant from the anti-angiogenin IgG labelled Protein G Dynabeads following incubation with the milk derived fraction.

The inventors have recognised the need for methods which allows the enrichment and isolation of angiogenin in an efficient manner from a readily available starting material, milk, particularly bovine milk. Certain of these methods provide a highly purified angiogenin fraction on a research scale and others provide commercially viable enrichment processes.

The first and second aspects provide a method wherein the angiogenin protein present in a milk sample is separated away from other proteins and material present in the sample by means of a capture agent which interacts with the angiogenin protein.

In a further embodiment of the first or second aspect, prior to contacting the milk sample with the contact agent, the milk sample is added to a preliminary and separate support in the absence of the capture agent or antibody, wherein material present in the milk sample which interacts non-Specifically with the support is removed from the milk sample.

In one embodiment of the first or second aspect the support is polymeric- and/or agarose-based. For example the support may be Dynabeads Protein G.

In a further embodiment of the first or second aspect the antibody is a polyclonal antibody or a monoclonal antibody. Preferably the antibody is monoclonal. One suitable anti-bovine angiogenin antibody is monoclonal antibody clone number 1B14D4, acquired from the Department of Biochemistry, Chungbuk National University, Cheongju, Chungbuk, Korea.

In a still further embodiment of the first or second aspect the capture agent or antibody is immobilised to the support by covalent attachment thereto.

As used herein, the term "capture agent" refers to an entity which is capable of "interacting" with the angiogenin protein to form an angiogenin-capture agent complex. Preferably the interaction renders the angiogenin protein immobilised. Ideally, the capture agent is specific for only the angiogenin protein present in the milk sample; however, it would be understood by a person skilled in the art that other constituents in the milk sample may also interact non-specifically with the capture agent. A capture agent of choice is therefore one which displays minimal non-specific binding.

Suitable capture agents may include, but are not limited to, antibodies to angiogenin, peptides or proteins (including those which bind angiogenin, for example follistatin), chemical entities, receptors, ligands, aptamers, polysaccharides, lipids, hormones or the like. Preferably the capture agents are antibodies, or functional fragments thereof.

In one embodiment the capture agent is able to distinguish between RNAse 4 and angiogenin, despite their sequence identity of 30%.

The interaction between the capture agent and angiogenin should be reversible so that the angiogenin can be ultimately isolated away from the capture agent. The interaction can be direct or may be indirect such that the interaction of the capture agent with angiogenin is mediated by a third (or more) agent, for example a linker molecule, peptide, or the like, that brings the capture agent and angiogenin together.

In one embodiment the capture agent is attached or "immobilised" to a support. The term "support" as used herein refers to the material on which the capture agents are attached. The support may be a solid support. Examples of suitable supports include polymeric- and/or agarose-based matrix supports such as Sepharose, nitrocellulose, nylon, polyvinylidene difluoride (PVDF), glass, plastic, gels, sols, ceramics, metals, and derivatives of any of these.

Capture agents may be attached to a support directly or indirectly. Capture agents can be directly or indirectly deposited at high density on the support. For example, Protein A or G can be printed onto a support. Capture agents, such as antibodies to angiogenin, may then be coupled to the support through their interactions with Protein A or G. The advantage of this method is that by engaging the constant regions of antibodies with Protein A or G, the variable regions of the antibodies (angiogenin-binding domains) will be fully exposed to interact with angiogenin.

Capture agents may also be attached to a support which is a membrane made from polymeric, elastomeric or other suitable membrane material. Examples of such materials include, but are not limited to, PVDF, nitrocellulose, nylon or modified variants thereof. The invention contemplates the use of any such material such as is known to those of skill in the art for use in Northern, Southern or Western blotting. Particular aspects of membranes which are desirable for the purpose of the invention include the ability to bind large amounts of angiogenin protein, the ability to bind angiogenin protein with minimal denaturation, and the ability to minimise the binding of non-angiogenin constituents present in the milk sample.

The first and second aspects rely on a reversible affinity interaction between angiogenin and an angiogenin antibody which acts as the capture agent.

A method of the invention which uses antibodies in this way is commonly referred to as immunoaffinity chromatography. In this regard, the antibody specific for angiogenin is immobilised onto a support to yield an active immunosorbent. The active immunosorbent is then packed in a column ready to receive the heterogeneous protein sample to be purified. A milk sample containing a complex mixture of proteins is added to, or passed over, the immunosorbent whereby the angiogenin protein present in the sample interacts with the antibody to form an angiogenin-antibody complex, and the other proteins and material present in the sample are washed away in the column flow-through. The reversible interaction between the antibody and angiogenin is then disrupted to yield a highly purified product as an eluate from the column which is enriched for angiogenin.

As used herein, the terms "angiogenin antibody" or "antibody" encompass polyclonal and monoclonal antibody types.

Furthermore, the term "antibody" means intact immunoglobulin molecules, chimeric immunoglobulin molecules, or Fab or F(ab')$_2$ fragments. Antibodies, as defined herein, also include single chain antibodies (ScFv), which comprise linked V$_H$ and V$_L$ domains and which retain the conformation and specific binding activity of the native idiotope of the antibody. Such single chain antibodies are well known in the art, and can be produced by standard methods. The antibodies can be of any isotype, IgG, IgA, IgD, IgE and IgM. It will be clearly understood that the antibodies, or fragments thereof, encompass those which are currently known or may become known in the future.

Polyclonal antibodies to angiogenin can be obtained by techniques known in the art. For example polyclonal angiogenin antibodies can be obtained by immunising a rabbit or goat and purifying the immunoglobulin fraction from the resulting serum. The antibodies obtained represent a mixture of antibodies with a variety of specificities capable of binding to various, parts of the angiogenin protein which was used as the immunogen.

Polyclonal antibodies to angiogenin can also be purchased commercially (for example from Calbiochem, USA; LifeSpan Biosciences, USA; R&D Systems, USA).

Although polyclonal antibodies are easy to produce, they suffer from several disadvantages for use in immunoaffinity chromatography. For example, they are heterogeneous with respect to epitope specificity and binding properties, and antigen which is quite pure must be used to avoid raising unwanted antibodies to minor impurities in the protein preparation. Furthermore, the antibody preparation is not completely reproducible from one immunised animal to another making it difficult to obtain large quantities of consistent material. Therefore although angiogenin polyclonal antibodies can be used in the methods of the invention, they are not the antibody of choice.

Angiogenin monoclonal antibodies may be used. Monoclonal antibodies to angiogenin may be prepared using any technique which provides for the production of antibody molecules by continuous cell lines in culture. These include, but are not limited to, the hybridoma technique, the human B-cell hybridoma technique, and the EBV-hybridoma technique as would be known by one skilled in the art. Monoclonal antibodies to angiogenin can also be purchased commercially (for example Abcam, UK; GeneTex, USA; BACHEM, USA).

Monoclonal antibodies can be produced with smaller quantities of angiogenin as immunogen, which angiogenin need not be pure. Once a hybridoma cell line is established, it can be used to produce a potentially unlimited supply of antibody with reproducible properties. Furthermore, the monoclonal antibody will bind to a single epitope and will have homogeneous binding and elution properties.

The immunosorbent performance is dependent on the nature of the support to which the antibody is immobilised. A person skilled in the art would understand that efficient immunosorbents should ideally possess mechanical and physical stability, suitable flow properties, acceptable pressure drop, minimal non-specific binding, a large surface area for protein-antibody interactions, and chemical stability.

In this regard, polymeric- and/or agarose-based matrix supports such as Sepharose are commonly used, and are commercially available. Examples of suitable matrices for a support which is to be used in an immunoaffinity chromatography method of the invention include CNBr-activated Sepharose (GE Healthcare), Emphaze™ activated chromatography resin (Pierce Chemical), CM Bio-Gel A gel (Bio-Rad), ECH Sepharose 4B (GE Healthcare), Reacti-Gel 6X (Pierce Chemical), Protein A and G Sepharose CL 4B Beads (Pierce Chemical), HiTrap NHS-Activated (GE Healthcare), and AffiPrep 10 (Bio-Rad).

The efficient functioning of the immunosorbent column is dependent on the activation chemistry used to couple the antibody to the matrix, thereby immobilising the antibody. Typically, covalent coupling is employed. As would be known by the person skilled in the art, there are a number of different protocols for covalently binding antibodies to a solid-phase matrix; however, the easiest is coupling the antibodies to Protein A or protein G beads. Protein A or G matrices bind specifically to the F$_C$ domain of antibodies. After the antibody has bound, the interaction is stabilised by covalently cross-linking the antibody to the Protein A or G with a bifunctional coupling reagent.

Another method is to couple the antibody to matrix beads that have been chemically modified to contain an active group. The activated beads are mixed with the antibody, which interacts with the active sites to yield a covalent linkage. This method offers advantages over the use of Protein A or G matrices in that the beads can be activated in much harsher conditions than proteins can sustain, thus allowing the use of a range of activation protocols which are known in the art (see also Porath and Axén, 1976, *Methods Enzymol.* 44: 19 to 45; Scouten W H, 1987, *Methods Enzymol.* 135: 30 to 65). Further advantages of this approach include the wide range of activated beads that are commercially available, as evidenced above, and the fact that many of these coupling methods yield a linkage that is stable to a wide range of denaturing conditions.

Chemical modification of the matrix beads to generate active groups can be achieved a number of ways including treatment with carbonyldiimidozole, cyanogen bromide, N-hydroxysuccinimide (NHS), iodoacetyl and tresyl chloride.

Coupling between the activated beads and the angiogenin antibody is predominantly mediated through primary amino groups or sulfhydryl groups present on the antibody. As an example, antibody coupling (via amino groups) to an NHS-activated matrix such as AffiPrep to generate a functioning immunosorbent can be achieved in the following manner. An appropriate amount of activated AffiPrep matrix, supplied as a slurry of beads suspended in ethanol (50% v/v), is poured on a sintered glass funnel and the liquid is sucked through by gentle vacuum. The remaining suspension is stirred with a glass rod and kept moist at all times. The activated beads are washed with ice-cold distilled water to ensure the removal of all ethanol. The water is drained from the beads with gentle vacuum, and the moist beads are transferred to a flask containing 3-5 mg/ml angiogenin antibody solution in coupling buffer (0.1M 4-morthlinepropanelsulfonic acid (MOPS), 0.1M NaCl, pH 7.2). The contents of the flask are then mixed at low speed overnight in a cold-room or for 4 hours at room temperature. The coupling involves a reaction between an activated ester on the beads and a reactive amine on the antibody, which ultimately leads to the formation of a stable amide (covalent) linkage. After completion of the coupling step, the beads are allowed to settle at room temperature, and the supernatant is then removed by aspiration or decanting. Blocking solution (1M ethanolamine, pH 8.0) is then added to the immunosorbent and mixed at low speed for 1 hour at room temperature. Upon completion of the blocking step, the beads are again allowed to settle and the supernatant is removed. To ensure complete blocking of unused activated sites, the blocking step is repeated two additional times.

Ligand-coupling buffer (10 mM Tris HCl, 50 mM NaCl, pH 6.8) is then added to the antibody-coupled beads and the contents are mixed at low speed for 1 hour at room temperature. This step is preferably repeated four to five more times to ensure that all of the blocking solution is removed from the beads. The immunosorbent is then resuspended in an appropriate amount of ligand-coupling buffer and stored at 4° C. until needed. The immunosorbent is then ready for use and can be packed in columns by gravity for angiogenin binding.

Prior to addition of the milk sample to the column of prepared beads, the column may be "equilibrated" with a suitable wash buffer. Examples of appropriate wash buffers include, but are not limited to, those containing 10 mM Tris HCl and 50 mM NaCl at pH 7.0, those containing 10 mM Tris HCl, 140 mM NaCl, 0.5% Triton X-100 and 0.5% sodium deoxycholate at pH 8.0, those containing 10 mM Tris HCl, 140 mM NaCl and 0.5% Triton X-100 at pH 8.0, those containing 10 mM Tris HCl, 140 mM NaCl and 0.5% Triton X-100 at pH 9.0, and those containing 150 mM NaCl, 0.1% Triton X-100 and 50 mM triethanolamine. The column may be equilibrated with one or more of the above-listed wash buffers.

It is common practice, but not essential, that prior to addition of the milk sample to the equilibrated immunosorbent (antibody-containing) column, the sample is first run through a preliminary and separate "pre-column" which contains the same support as the immunosorbent column but which does not have antibody linked to the support. This is to further ensure that the sample is purged of material which is likely to bind non-specifically to the immunosorbent column. The pre-column is equilibrated prior to addition of the milk sample in the same manner as the immunosorbent column using wash buffers as described above.

It is further preferred that prior to adding the milk sample to the equilibrated immunosorbent column and pre-column (if utilised), fat is removed from the milk sample (often referred to as delipidation). However this is not essential. Fat can be removed by any conventional means known in the art, including low-speed centrifugation, separation or microfiltration. Optionally, caseins may also be removed prior to the immunoaffinity chromatography method, for example by microfiltration through a 1 micrometer membrane, rennetting or acid precipitation. If microfiltration is chosen, caseins will be retained by the membrane and whey proteins, including angiogenin, will move into the permeate.

If caseins are removed by microfiltration or other membrane process, the permeate is applied directly to the equilibrated immunosorbent column and pre-column (if utilised), or optionally the permeate may be concentrated prior to application. Suitable methods of concentration include filtration (such as ultrafiltration with a 0.5-10 kDa membrane, nanofiltration with a 150-500 Da membrane, or reverse osmosis allowing only water to permeate the membrane), or freeze-drying followed by resuspension in a wash buffer as described above.

The milk sample (crude or pre-conditioned) is typically added to the pre-column and/or primed immunosorbent column (i.e. the solid support) at a flow rate of 0.2 to 2 column volumes per hour. However, a flow rate of up to 5 column volumes per hour is also appropriate. Once the entire sample has been added, a series of wash steps follows using any one or more of the wash buffers disclosed above. The wash buffers are applied until the wash which has passed through the column is at a baseline absorbance at 280 nm. This indicates that there is no further un-bound protein to be washed from the column.

Separation of the angiogenin which is bound to the solid support via the antigen (capture agent) can be achieved in a variety of ways depending on the nature of the solid support used. It is important that separation conditions which might denature the angiogenin are avoided. As would be understood by a person skilled in the art, a range of available separation strategies can be considered when selecting an appropriate separation protocol. These may include acid separation, base separation and the use of chaotropic agents.

Acid separation is the most widely used method and is usually very effective. Commonly used acids include glycine-HCl, pH 2.5, 0.02M HCl and sodium citrate, pH 2.5. However, in order to avoid acid-induced denaturation, upon separation the pH of the separated sample must be quickly neutralised to pH 7.0 with 2M Tris base, pH 8.5. Base separation typically relies on separants consisting of 1M $NH_4OH$, 50 mM diethylamine, pH 11.5 or 50 mM triethanolamine solution containing 150 mM NaCl and 0.1% Triton X-100.

Chaotropic agents disrupt the tertiary structure of proteins and therefore can be used to disrupt the angiogenin:antibody complexes. Chaotropic salts are useful as they disrupt ionic interactions, hydrogen bonding and sometimes hydrophobic interactions. Effective chaotropic anions include $SCN^-$, $ClO_4^-$, $I^-$, $Br^-$, and $Cl^-$. Effective chaotropic cations include Mg, K and Na. Separants such as 8 M urea, 6 M guanidine-HCl and 4 M NaSCN are effective in disrupting most antibody:antigen interactions. However to minimise chaotropic salt-induced protein denaturation, rapid desalting or dialysis of the separant is advised.

Sample separated from the solid support is collected and analysed for the presence of angiogenin and in order to determine the extent of angiogenin enrichment. Suitable analysis steps include densitometric analysis of stained SDS-PAGE to compare the angiogenin specific protein band abundance to any contaminating proteins present, mass spectrometry such as MALDI-TOF/TOF MS, immunoaffinity detection such as western blotting or ELISA, amino acid analysis and sequencing, cation exchange chromatography, and reversed-phase chromatography. Each of these techniques would be known to the person skilled in the art.

The third aspect provides a method wherein the constituents (including angiogenin) of the milk sample (as provided in a liquid phase) are added to a second phase which is capable of separating the constituents of the milk sample from each other based on the size of the constituents. Separated angiogenin can then be collected; essentially providing a product enriched for angiogenin.

As used herein, reference to "size" in the context of a constituent of milk, including angiogenin, should also be taken as reference to the "hydrodynamic diameter" or "hydrodynamic volume" of the constituent. The "hydrodynamic diameter" or "hydrodynamic volume" of a constituent refers to the diameter or volume the constituent assumes when it is in motion in a liquid form.

A "second phase" in the context of the present invention is taken to mean any mechanism by which individual constituents of the milk sample can be separated based on the size of each constituent.

In one embodiment the second phase is a semi-permeable phase. By "semi-permeable phase" is meant a non-aqueous phase to which the constituents of the milk sample can interact with and either pass through or be retained by the phase.

The term "permeate" refers to the constituents of the milk sample which have passed through or permeated the second phase.

The term "retentate" refers to the constituents of the milk sample which have been retained by the second phase.

For example the semi-permeable phase may be a membrane or filter, or the like, which acts a molecular sieve by separating the milk constituents according to size based on the relative porosity of the phase.

In the context of the present invention, a constituent that is "retained" by the second phase is essentially trapped or is prevented from passing through the second phase. A constituent that is retained by the second phase will be part of the retentate which can be removed from the second phase, it just cannot pass through the second phase. A constituent that passes through the second phase is collected as the permeate.

In one embodiment, the second phase is a semi-permeable membrane. In the context of the present invention, the term "membrane" is synonymous with the terms "mesh" and "filter" and the like. The membrane may be made of any material which renders the membrane semi-permeable or "porous", i.e. able to allow or prevent the passage of molecules through the material, based on the size of the pores, holes, or the like, in the membrane. For example, suitable materials include, but are not limited to, thermoplastics such as polysulfone (PSU), polyether sulphone (PES), cellulose acetate, nylon, polyvinylidene fluoride (PVDF), polytetrafluoroethylene (PTFE), polycarbonate, polyetherimide, and polyacrylonitrile. Such membranes may be purchased commercially, from sources such as Millipore, Sartorius, GE Healthcare (Osmonics), Koch Membrane Systems.

With respect to the method of the third aspect, a second phase would be chosen which allows the passage of angiogenin through the second phase, but prevents the passage of molecules larger than angiogenin. For example, any second phase with a molecular weight cut-off between 20 kDa and 50 kDa would be acceptable.

The term "molecular weight cut-off" is taken to indicate the maximum molecular size of a component which is capable of passing through the second phase. In a preferred embodiment, the optimum second phase would be one with a molecular weight cut-off of 30 kDa.

It would be appreciated that one or more additional rounds of purification can be employed using the methods of the present invention. The purpose of the one or more purification rounds is to further concentrate the angiogenin obtained from an initial purification, and to lower the concentration of unwanted contaminants. In this regard, the additional one or more rounds of purification may utilise a second phase which has a molecular weight cut-off smaller than the size of angiogenin, for example a second phase with a molecular weight cut-off of 5 kDa or 10 kDa may be chosen. In this way, angiogenin will be prevented from passing through the second phase and will be retained by the second phase. The purified angiogenin retained by the second phase can then be dried if desired using methods such as freeze-drying or spray-drying.

Pressure can be applied to the milk sample after it has been added to the second phase so that it is essentially forced through the second phase. Force may be applied by any mechanism which provides a pressure of no more than 290 psi (20 Bar), more preferably 218 psi (15 Bar), and even more preferably 145 psi (10 Bar).

For example, the force may be a force applied by a syringe, compressed gas (i.e. a stirred cell), a pump, a centrifuge, or any practical combination thereof. Ideally the force is applied from a cylinder of compressed nitrogen at a pressure of 70 psi (5 Bar).

Variations of the method of the third aspect may also make use of a binding agent which is specific for the angiogenin protein. The principle is that the combination of angiogenin and the binding agent will render the combination larger in size than angiogenin alone. Therefore angiogenin, when complexed with the binding agent, can be separated from those milk constituents which have a similar size using the methods of the third aspect. In this regard, a second phase would be chosen which retains the angiogenin-binding agent complex and allows other components of the milk sample which are smaller in size than the complex to pass through the second phase.

The interaction between the binding agent and angiogenin should be reversible so that the angiogenin can be ultimately separated from the binding agent by using the methods of the invention. In this instance, a second phase would be chosen which allows this separation bearing in mind the relative size of the binding agent and angiogenin. Therefore angiogenin may be retained by the second phase or allowed to pass through the second phase, and vice-versa for the binding agent.

Any other variations of the method of the third aspect are also considered within the scope of the invention. For example, the method according to the third aspect may be used initially, wherein no binding agent is present. However, the product which comprises angiogenin may be combined with a binding agent such that angiogenin-binding agent complexes form. The product can then be added to a further second phase in order to remove non-angiogenin components present in the product. Following this, the interaction between the binding agent and angiogenin can be reversed and the components separated by application to a further second phase.

As used herein in relation to the third aspect, the term "binding agent" is an entity which is capable of interacting with or forming a complex with, and retaining, the angiogenin protein. The terms "retain" or "retaining" in this context are taken to mean to hold or bind the angiogenin protein. Ideally, the binding agent is specific for only the angiogenin protein present in the milk sample; however, it would be understood by a person skilled in the art that other constituents in the milk sample may also interact non-specifically with the binding agent. A binding agent of choice is therefore one which displays minimal non-specific binding.

Suitable binding agents may include, but are not limited to, antibodies to angiogenin, peptides or proteins (including those which bind angiogenin, for example follistatin), chemical entities, receptors, ligands, polysaccharides, lipids, polymers such as DEAE dextran, hormones or the like. Preferably the binding agent is an antibody, or functional fragment thereof.

The interaction can be direct or may be indirect such that the interaction of the capture agent with angiogenin is mediated by a third (or more) agent, for example a linker molecule, peptide, or the like, that brings the capture agent and angiogenin together.

The terms "antibodies to angiogenin" or "antibody" encompass polyclonal and monoclonal antibody types having the same meaning in relation to the third aspect as they do in relation to the first and second aspects as described above.

Permeate or retentate collected following the separation step of the method of the third aspect may be analysed for the presence of angiogenin and in order to determine the extent of angiogenin enrichment.

The fourth aspect provides another method wherein the constituents (including angiogenin) of the milk sample, are separated from each other based on their size. A method as described in accordance with the fourth aspect is commonly referred to as size exclusion chromatography.

As used in relation to the fourth aspect, the term "size" has the same meaning as described above in relation to the third aspect.

The term "size exclusion chromatography" encompasses methods referred to as gel permeation, gel permeation chromatography, gel filtration or gel filtration chromatography. Henceforth, any reference to "size exclusion chromatography" should also be taken to include any of the terms specified above, or any other similar chromatographic process for separating proteins from other proteins or other biomolecules based on their size.

The principle of the method of the fourth aspect is that it provides a process in which constituents in solutions of a milk sample are allowed to come into contact with a second phase, wherein the second phase influences the rate of flow of the constituents of the product as they interact with and/or pass through the second phase based on the size of the constituents. The constituents of the product become separated because movement of the various constituents present in the sample is retarded as a result of the constituents becoming "entrapped" by, and subsequently released from, the second phase.

A "second phase" in the context of the present invention is taken to mean any mechanism by which movement of the individual constituents of the milk sample can be manipulated based on the size of each constituent.

In relation to the fourth aspect, the second phase may be a solid phase. By "solid phase" is meant a non-aqueous matrix to which the constituents of the milk sample can interact with and/or pass through. The solid phase may be a purification column, a discontinuous phase of discrete particles, a resin, a membrane, or filter etc. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above.

In one embodiment of the fourth aspect, the second phase is a resin which may be packed into a chromatographic column. In this regard, the entrapment may take place by constituents entering pores present in the resin. Molecules larger than the pore diameter cannot enter those pores and emerge quickly from the column, whereas smaller molecule enter the pores of the resin, and take longer to make their way through the column. The rates of entrapment and subsequent release vary from constituent to constituent, therefore giving rise to the phenomenon of separation by size exclusion.

If the second phase is composed of a porous resin, ideally the porous structure must be well-defined and reproducible from batch-to-batch, and the distribution of pore sizes and shapes should be as narrow as possible. Furthermore, the ratio of the total pore volume to the void volume of the column which contains the resin should be as high as possible to widen the window available for the separation, and therefore improve the peak capacity. The separation efficiency can be further enhanced if the resin size is small (for example, 5 μm or less) and regular. Finally, the resin column should ideally have a diameter greater than 5 mm, it should be long (any length greater than 100 mm), and should be densely packed with resin.

The resin may be composed of polyacrylamide, dextran, agarose, silica or cross-linked polystyrene. Examples of resins suitable for size exclusion chromatography may include, but are not limited to Superose (GE Healthcare), Sephadex (GE Healthcare), Sephacryl (GE Healthcare), TSK-GEL® $H_{HR}$ (Tosoh Biosciences), Toyopearl HW (Tosoh Biosciences) and TSK-GEL PW (Tosoh Biosciences), Ultrogel® AcA (IBF Biotechnics, Inc) and Bio-Gel A (Bio-Rad). The most appropriate resins would be those giving good separation of proteins with a molecular weight of between 10 kDa and 20 kDa. Examples of suitable resins include Superose 12, Sephadex 75, Sephacryl S-100HR, Toyopearl HW-50, TSK-GEL PW-50, Ultrogel® AcA 54 and Bio-Gel A 1.5M. Most preferably, the resin will be Sephacryl S-100HR.

With respect to preparation ("equilibration") of the resin for separation, and the separation process itself, the ideal buffer to be used should be of a low osmolarity and have a neutral pH. Ideally, suitable buffers include water, phosphate buffer, phosphate-buffered saline, but other buffers with similar properties may also be used.

However, because angiogenin is a very stable protein and can refold after denaturation, a suitable buffer could also have either a very low or very high pH, have a high osmolarity, or contain denaturing agents (e.g. sodium dodecyl sulphate, urea or guanidine), which can be removed latter without affecting the bioactivity of the angiogenin.

The chromatographic column is ideally equilibrated by passing greater than 2 column volumes (CV) of buffer through the column prior to applying the milk sample. The flow rate during equilibration will range from 0.1 to 3 CV/h. Preferably, the flow rate will be 0.66 CV/h, although 1 CV/h would be acceptable if the pressure does not exceed that tolerated by the resin. The flow rate during separation will also range from 0.1 to 3 CV/h. Preferably the flow rate will be 0.375 CV/h, though acceptable separations may be gained by flows up to 0.66 CV/h.

The volume of sample applied to the equilibrated column may range from 0.005 to 0.2 CV, ideally 0.015 CV to up to 0.05 CV. The amount of protein present in the applied sample may range from 0.001 to 0.2 g protein/mL CV, ideally 0.0016 g protein/mL CV up to 0.05 g protein/mL CV.

Separation typically occurs over approximately 1-2 hours under the conditions described above. Ideally, the separated sample fractions which exit the column are monitored by a UV spectrophotometer at 280 nm. Angiogenin elutes after the immunoglobulins, lactoferrin and lactoperoxidase, but before most growth factors. Fractions should be collected to ensure that the angiogenin is captured. The overlapping lactoferrin and lactoperoxidase peaks will be visible as a green-brown band and collection does not need to start until after the green-brown band has exited. If all β-lactoglobulin has been removed by the column, then the next peak will be angiogenin.

A fifth aspect provides a method for providing a product enriched for angiogenin from milk, in which method the angiogenin protein present in a milk sample is separated or fractionated from other proteins present in the sample according to angiogenin's charge and electrophoretic mobility as the milk sample flows through an electric field. The milk sample is therefore provided as an "aqueous milk flow".

Fractions of the milk flow to which the electric field has been applied are recovered, and those fractions enriched for angiogenin are identified.

The method according to the fifth aspect relies on the use of an electric field to separate a heterogeneous population of proteins according to their electrophoretic mobilities or isoelectric points. The technique further relies on the separation of the proteins in a carrier-free medium, i.e. a liquid (aqueous) medium in the absence of a stationary phase (or solid support material) to minimise sample loss by adsorption. Such a technique is commonly referred to as free flow electrophoresis.

A method of the fifth aspect may be performed in an electrophoretic chamber which is formed by two narrowly spaced plates positioned parallel to each other. The plates are flanked by two electrodes (anode and cathode) which generate a high-voltage electric field between the plates. A buffer medium, commonly referred to as a "separation buffer", flows through the chamber at a constant speed, wherein the electric field is applied in a direction transverse to the flow of both the buffer medium and milk sample to be purified.

In the context of the fifth aspect, "transverse" refers to the application of an electric current to the buffer medium and milk sample flow at an angle (i.e. not parallel) or in a different plane thereto.

The sample to be analysed is applied to the charged field, and under laminar flow the sample is transported within the buffer medium between the two plates. Charged particles are deflected dependent on their charge properties, allowing for subsequent separation. Since each protein has a different charge quantity, its electrophoretic mobility is also different in the electric field. Therefore, each protein is deflected and separated while it flows through the electrophoretic chamber in the separation buffer in conjunction with the flowing velocity of the separation buffer. This method can be used to continuously separate proteins and hence is effective for the separation and purification of angiogenin on an industrial scale.

A number of free flow electrophoresis techniques are known in the art, each one distinguished on the basis of their mode of species separation. For example, species may be separated according to their pI (isoelectric focussing), net charge density (zone electrophoresis), and electrophoretic mobility (isotachophoresis, field step electrophoresis and field flow fractionation).

Free flow electrophoresis techniques may be performed in various modes, including for example continuous or transiently stopped (interval) modes. In continuous mode applications the milk sample is applied continuously into the chamber, whereby angiogenin is separated from other components of the sample under the continuous flow of the buffer medium (separation buffer) and the uninterrupted application of the electrical field during the entire separation process. In interval mode, the milk sample and separation buffer are introduced into the separation space or "zone" of the chamber, followed by a separation process where the bulk flow of the medium including the sample is halted while applying the electrical filed to achieve separation. After separation/fractionation of the sample, the electrical field is turned off or reduced to be ineffective and the bulk flow is again turned on so that the fractionated sample is driven through the chamber and subsequently collected.

The free flow electrophoresis techniques can also be performed under denaturing conditions, for example by the addition of urea or suitable detergents known in the art. It will be appreciated by a person skilled in the art that the pI of angiogenin will be similar to the pI in its native state.

A method of the fifth aspect may encompass each of the above-mentioned free flow electrophoresis techniques. Preferably, angiogenin is separated from the milk sample according to its pI in a continuous mode.

In this regard, as would be understood by a person skilled in the art, a suitable buffer medium, i.e. separation buffer, may include but is not limited to binary buffer systems (A/B media), commercial ampholytes such as Servalyt® (Serva, Germany), complementary multi-pair buffer systems such as Prolyte Separation Buffers I and II (Becton Dickinson Diagnostics, Germany), and volatile buffer systems. Furthermore, a list of separation media suitable for free flow electrophoresis is provided in the book, "Free-flow Electrophoresis", published by K. Hanning and K. H. Heidrich, (ISBN 3-921956-88-9).

For the separation of angiogenin according to its pI, the buffer medium chosen will be suitable to form a pH gradient in the separation space of the chamber. In this regard, Prolyte Separation Buffers I and II are preferred. Separation Buffer I contains 29% IEF Prolyte Buffer 2 and Separation Buffer II contains 17% Prolyte Buffer 2, 50 mM HEPES and 42 mM 6-aminohexanoic acid.

The term "pH gradient" implies that there are no abrupt boundaries observed with respect to pH. Under this definition, a graph of a pH gradient in an isoelectric focussing device would be shown as a relatively smooth curve with no sharp transitions for the portions of interest. For the separation of angiogenin, the gradient is preferably in the pH range of 8 to 11.

The method according to the fifth aspect may be improved by incorporation of stabilisation media and counter-flow media. For example, a counter-flow medium may be introduced into the separation space counter to the continuous flow direction of the bulk separation buffer and sample that travels between the electrodes.

Stabilising media may be used to stabilise the conditions within the separation space formed by for example suitable binary buffer systems. A suitable stabilising medium therefore also acts as a "reservoir" supplying or replacing the ions in the separation zone.

The term "stabilising medium" as used herein refers to a medium composed of two components. The first is a cathodic stabilisation medium and the second is an anodic stabilisation medium. The cathodic or anodic stabilisation medium may comprise a monoprotic acid and/or a monobasic base. A person skilled in the art would understand that the ions formed in the stabilisation media should have sufficiently low electrophoretic mobilities.

For the efficient separation and purification of angiogenin, a suitable anodic stabilisation medium consists of 100 mM sulphuric acid, 50 mM acetic acid, 100 mM DL-2-aminobutyric acid and 30 mM glycyl-glycine, and a suitable cathodic stabilisation medium consists of 100 mM sodium hydroxide, 30 mM ethanolamine and 300 mM β-alanine.

Suitable apparatus to conduct the free flow electrophoresis methods of the present invention are commercially available. For example the Becton Dickinson FFE System (BD Diagnostics, Germany).

It is preferred that prior to adding the milk sample to the electric field, fat is removed from the milk sample (often referred to as delipidation); although this is not essential. Methods for delipidation are known in the art and examples of such methods are described below. Optionally, caseins may also be removed prior to the free flow electrophoresis method, using methods know in the art, with examples of such methods also provided below.

If caseins are removed by microfiltration or other membrane process, the permeate is applied directly to the free flow electrophoresis apparatus or optionally the permeate may be concentrated prior to application: Suitable methods of concentration include filtration (such as ultrafiltration with a 0.5-10 kDa membrane, nanofiltration with a 150-500 Da membrane, or reverse osmosis allowing only water to permeate the membrane), or freeze-drying followed by resuspension in a buffer compatible for free flow electrophoresis.

It is preferred that prior to conducting the methods of the third, forth or fifth aspects, fat is removed from the milk sample (often referred to as delipidation). However, this is not essential. Fat may be removed by any conventional means known in the art, including low-speed centrifugation, separation or microfiltration.

The fat-depleted milk sample may optionally be subject to a further "conditioning" step prior to conducting the methods of the third, fourth or fifth aspects. Such a step may include passing the sample through an anion exchange column. Such methods are known in the art. For example, an anion exchange column may be filled with a resin with functional groups such as DEAE (Diethylaminoethyl), Q (Quaternary ammonium), QAE (Diethyl-(2-hydroxypropyl)aminoethyl) attached to a suitable support, such as cellulose, polyacrylamide, dextran, agarose, silica or cross-linked polystyrene. The fat-depleted milk sample would be passed across the column at a flow rate of 10 CV/h (though up to 1000 CV/h may be used) until 10 CV fat-depleted milk was applied (though between 0.1 CV and 50 CV may be used). It would be expected that proteins such as β-lactoglobulin, α-lactalbumin and bovine serum albumin would be removed. The proteins remaining in the chromatographed sample would be primarily lactoferrin (LF), lactoperoxidase (LP), and immunoglobulins; however, angiogenin would also be present at a concentration of <1% w/w protein and this could be further purified.

In another embodiment of each of the first to fifth aspects, the milk sample is heated prior to carrying out the method. Heating the milk sample may reduce the amount of lactoperoxidase and other proteins that denature at lower temperature than angiogenin in the sample and thus improves the amount of angiogenin.

Fractions obtained from the methods of the first to fifth aspects may be analysed for the presence of angiogenin and in order to determine the extent of angiogenin enrichment. Suitable analysis steps include densitometric analysis of stained SDS-PAGE to compare the angiogenin specific protein band abundance to any contaminating proteins present, mass spectrometry such as MALDI-TOF/TOF MS, immunoaffinity detection such as western blotting or ELISA, amino acid analysis and sequencing, cation exchange chromatography, and reversed-phase chromatography. Each of these techniques would be known to the person skilled in the art.

The methods according to any one of the first to fifth aspects may be performed in isolation to obtain a product enriched for angiogenin, or may be incorporated as part of an integrated fractionation process in which other desired milk product components are fractionated.

The product enriched for angiogenin obtained by the methods of any one of the first to fifth aspects may be further treated to remove residual non-angiogenin proteins and/or to remove salt. This may be considered important for the production of standardised food substances or nutraceuticals, and for the preparation of pharmaceutical grade angiogenin. Such steps may be achieved by cation exchange chromatography, one or more further free flow electrophoresis steps, immunoaffinity chromatography, membrane filtration, ideally ultrafiltration, or equivalent as would be known in the art, e.g. dialysis, electrodialysis, size-exclusion chromatography, solid-phase extraction, nanofiltration or other known means. It would be understood by the person skilled in the art that when angiogenin is used for the production of a food substance or nutraceutical, its purity need not be as high as that required for the production of a pharmaceutical or veterinary composition. For example, angiogenin purified to a level of 60% may be considered acceptable.

Since angiogenin is involved in a number of physiological functions, the enrichment of this protein using the method according to the invention provides an ideal and economical source of the protein which can subsequently be directed towards these functions. For example the purified protein may be used in the preparation of a food substance, nutraceutical, pharmaceutical or veterinary product.

In a still further embodiment of any of the first to fifth aspects, caseins are removed from the milk sample before or during the method. Proteins in the milk sample may also be concentrated prior to or during the method.

A suitable milk sample may include whole milk, skim milk, buttermilk, whey (such as acid or cheese/rennetted whey or permeate from microfiltration of milk or skim milk) or a whey fraction (such as whey protein concentrate or whey protein isolate flow through), and colostrum.

It will be apparent to those skilled in the art that the milk sample may be obtained from any lactating animal, e.g. ruminants such as cows, sheep, buffalo, goats, yaks and deer, non-ruminants including horses and donkeys, primates such as a human, and monogastrics such as pigs. The animal may be a transgenic animal, particularly an animal modified to express more angiogenin in its milk than the equivalent wild type animal.

It is preferred that skim milk which is derived from whole cow's milk, optionally from a transgenic cow over expressing angiogenin in its milk, is used as the milk sample in any one of the methods of the first to fifth aspects.

Furthermore, it has been shown that in bovine milk, angiogenin is present in the highest or most concentrated amount (up to 12 mg/liter) within the first 1 to 14 days of lactation. Following this, the concentration falls to a base level of approximately 1 to 2 mg/liter. Therefore it is preferred that cow's milk which is obtained within the first 14 days of lactation is used in the method of the present invention. Given the residual angiogenin levels in cows milk from later lactation, it may still be used a source for enriching angiogenin.

The terms "product enriched for angiogenin" is taken to mean that the angiogenin protein:total protein ratio present in the product is increased relative to the ratio present in the milk sample before the method is performed. For the product to be considered enriched for angiogenin, it should have an angiogenin content of at least 2% w/w, at least 10% w/w, at least 20% w/w, at least 30% w/w, at least 40% w/w, at least 50% w/w, at least 60% w/w, at least 70% w/w, at least 80% w/w, at least 90% w/w, at least 95% w/w or at least 99% w/w.

The term "product" in the context of the methods of the first to fifth aspects is not intended to limit the invention to the production of angiogenin-enriched end products. The angiogenin-enriched product produced by the methods of the invention may be used as a starting or intermediate product in the production of other products.

As used herein, the term "fraction" refers to a partially purified portion of the milk sample.

Use of the term "efficient and commercially viable" is taken to mean an inexpensive and quick method when compared to methods which are currently employed to enrich for angiogenin.

Typical food substances that would benefit from the presence of angiogenin include sports nutrition supplements, infant food supplements, or food supplements for the frail, diseased or elderly.

The term "nutraceutical" as used herein refers to an edible product isolated or purified from food, in this case from a milk sample, which is demonstrated to have a physiological benefit or to provide protection or attenuation of an acute or chronic disease or injury when orally administered. The nutraceutical may thus be presented in the form of a dietary preparation or supplement, either alone or admixed with edible foods or drinks.

The food or nutraceutical composition may be in the form of a soluble powder, a liquid or a ready-to-drink formulation. Alternatively, the food or nutritional composition may be in solid form; for example in the form of a ready-to-eat bar or breakfast cereal. Various flavours, fibres, sweeteners, and other additives may also be present.

The food or nutraceutical preferably has acceptable sensory properties (such as acceptable smell, taste and palatability), and may further comprise vitamins and/or minerals selected from at least one of vitamins A, B1, B2, B3, B5, B6, B11, B12, biotin, C, D, E, H and K and calcium, magnesium, potassium, zinc and iron.

The food or nutraceutical composition may be produced as is conventional; for example, the composition may be prepared by blending together the protein and other additives. If used, an emulsifier may be included in the blend. Additional vitamins and minerals may be added at this point but are usually added later to avoid thermal degradation.

If it is desired to produce a powdered food or nutraceutical composition, the protein may be admixed with additional components in powdered form. The powder should have a moisture content of less than about 5% by weight. Water, preferably water which has been subjected to reverse osmosis, may then be mixed in to form a liquid mixture.

If the food or nutraceutical composition is to be provided in a ready to consume liquid form, it may be heated in order to reduce the bacterial load. If it is desired to produce a liquid food or nutraceutical composition, the liquid mixture is preferably aseptically filled into suitable containers. Aseptic filling of the containers may be carried out using techniques commonly available in the art. Suitable apparatus for carrying out aseptic filling of this nature is commercially available.

The product enriched for angiogenin obtained by the method of the present invention may also be formulated in a pharmaceutical composition or veterinary composition suitable for administration to a subject.

Preferably the composition also comprises one or more pharmaceutically acceptable carriers, diluents or excipients. Such compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives. Compositions of the present invention may be formulated for intravenous administration, topical application or oral consumption.

The term "subject" as used herein refers to any animal having a disorder which requires treatment or prophylaxis with a pharmaceutically-active agent. The subject may be a mammal, preferably a human, or may be a non-human primate or a non-primate animal such as those used in animal model testing.

While it is particularly contemplated that the angiogenin enriched product is suitable for use in medical treatment of humans, it is also applicable to veterinary treatment, including treatment of companion animals such as dogs and cats, and farm animals such as horses, ponies, donkeys, mules, llama, alpaca, pigs, cattle and sheep, or zoo animals such as non-human primates, felids, canids, bovids and ungulates.

The angiogenin enriched product may be administered to a subject in a manner appropriate to the disease to be treated and/or prevented. The quantity and frequency of administration will be determined by such factors as the condition of the subject and the type and/or severity of the subject's disease. Appropriate dosages may also be determined by clinical trials. An effective amount of the composition can be determined by a physician with consideration of individual differences in age, weight, disease severity, condition of the subject, route of administration and any other factors relevant to treatment of the subject. Essentially, an "effective amount" of the composition is an amount which is sufficient to achieve a desired therapeutic effect.

In another aspect, the present invention provides methods for the treatment and/or prevention of diseases. Such treatment methods comprise administering to a subject an effective amount of a nutraceutical, pharmaceutical composition or veterinary composition as described above. Preferably such diseases include those caused by viruses, bacteria, or fungi and their toxins. However since angiogenin plays a role in angiogenesis, diseases where the stimulation of angiogenesis is required may also be treated using an angiogenin-containing composition of the invention. These diseases include coronary artery disease, stroke, ischaemic limb disease, and delayed wound healing.

The terms "treating" and "treatment" as used herein refer to reduction in severity and/or frequency of symptoms, elimination of symptoms and/or underlying cause, prevention of the occurrence of symptoms (prophylaxis) and/or their underlying cause, and improvement or remediation of damage. Thus, for example, the present method of "treating" a disorder encompasses both prevention of the disorder in a predisposed individual and treatment of the disorder in a clinically symptomatic individual.

"Treating" as used herein covers any treatment of, or prevention of a condition in a vertebrate, a mammal, particularly a human, and includes: inhibiting the condition, i.e., arresting its development; or relieving or ameliorating the effects of the condition, i.e., cause regression of the effects of the condition.

"Prophylaxis" or "prophylactic" or "preventative" therapy as used herein includes preventing the condition from occurring or ameliorating the subsequent progression of the condition in a subject that may be predisposed to the condition, but has not yet been diagnosed as having it.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

EXAMPLES

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1

Method of Obtaining a Product Enriched for Angiogenin from Skim Milk Using a Method According to the First and Second Aspects (Immunoaffinity Chromatography)

The method of immunoaffinity chromatography has been broadly described previously but not in the context of angiogenin purification (see for example Subramanian A, 2002, *Molecular Biotechnology*, 20: 41-47).

The applicants of the present invention have shown that angiogenin can now be extracted from a milk sample using methods disclosed herein.

The immunoaffinity chromatography method employed in this example is performed using monoclonal antibodies to angiogenin obtained from a suitable source, e.g. Monash Antibody Technology Facility, Australia.

A 10 cm deep column was packed with SP Sepharose Big Beads (GE Healthcare) such that the total bed volume of the column was 29.7 L. To the column a flow of skimmed cow's milk was applied at a linear flow rate of 331 cm/h (34 liters of skimmed milk per liter of resin per hour) for 2 hours until the volume of skimmed milk applied was 68 times the volume of the resin packed into the column.

The milk remaining in the column was removed by adding 2.5 column volumes (CV) of water at a linear flow rate of 147 cm/h (15 liters of buffer per liter of resin per hour), or 0.25 CV/min, for 10 min.

The immunoaffinity chromatography method employed in this example was performed using monoclonal antibodies to angiogenin. The anti-bovine angiogenin antibody used here was a monoclonal antibody clone number 1B14D4, acquired from the Department of Biochemistry, Chungbuk National University, Cheongju, Chungbuk, Korea. The anti-human angiogenin antibody used here was monoclonal antibody clone number 14017 (R&D systems Incorporated).

Figure 2:
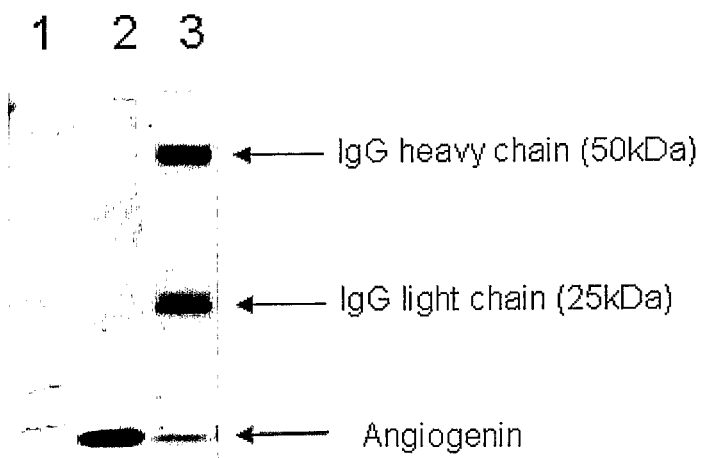
FIG. 2 shows western blot analysis of angiogenin following immunoaffinity purification. Angiogenin was detected using 0.5 µg anti-bovine mouse monoclonal (clone 1B14D4), secondary antibody was IRDye 800 CW goat anti-mouse IgG (Licor) and the image was taken on an Odyssey infrared imager (Licor). Lanes are 1) molecular weight standard, 2) milk derived fraction, 3) the eluant from the anti-angiogenin IgG labelled Protein G Dynabeads following incubation with the milk derived fraction

The solid support was Dynabeads Protein G (Invitrogen). The angiogenin antibody was coupled covalently to the beads using the following protocol. The Protein G Dynabeads were prepared for affinity purification by brief vortexing for 20 seconds. After vortexing, 50 μL of the resuspended IgG Dynabeads were transferred from the storage solution (Invitrogen). Using the magnet stand, the Protein G Dynabeads were sedimented for 1 minute. The supernatant was removed and the Protein G Dynabeads were then washed in 200 μL W&B buffer (0.1M Sodium phosphate buffer containing 0.01% Tween 20, pH 8.2). This process was repeated. W&B buffer (200 μL) containing approximately 5 μg bovine or human anti-angiogenin mouse monoclonal antibodies was added to the Protein G Dynabeads. This solution was incubated at room temperature for 10 minutes with rotation. The Protein G Dynabeads were sedimented and the supernatant removed. The IgG labelled Protein G Dynabeads were washed with 200 μL W&B buffer. The IgG labelled Protein G Dynabeads were sedimented and the supernatant washing buffer was removed. This washing step was repeated. To elute bovine angiogenin, denaturing conditions were used. The bovine angiogenin adsorbed IgG labelled Protein G Dynabeads were resuspended in 20 μL of 1× NuPAGE LDS Sample Buffer (Invitrogen; containing 2% lithium dodecyl sulphate and 2-mercaptoethanol) and heated for 10 min at 70° C. The Dynabeads were placed on the magnet and the sample was removed and loaded onto a 1-D gel for protein staining (FIG. 1) and western blot analysis (FIG. 2).

Example 2a

Method of Obtaining a Product Enriched for Angiogenin from Skim Milk Using a Method According to the Third Aspect (Ultrafiltration)

Bovine skim milk was applied to a column packed with SP (sulphopropyl) Sepharose until the volume of milk applied was 70 times the volume of the resin packed into the column (up to 1000 CV may be applied). The milk remaining in the column was removed with 6 CV water (a buffer of low ionic strength, <0.008M NaCl or equivalent) for 10 min. The fraction containing whey growth factors was eluted from the column with 6 CV buffer containing sodium ions equivalent to 0.4-0.5M NaCl (though other cations would be suitable), most preferably 0.4M NaCl. A pH in the range 5.5-7.5 provides the highest WGFE yields. The WGFE was desalted by means of diafiltration in an ultrafiltration plant fitted with 5 kDa membranes and dried by freeze-drying.

WGFE (1 g) was dissolved in 50 mL water containing 0.2% Triton X-100. The solution was applied to a membrane with a 30 kDa molecular weight cut-off (Viva Spin) and centrifuged at 8,000×g for 1.5 h at 20° C.

Protein concentration in the permeate and the retentate was determined using the 2D-Quant kit (GE Healthcare). Protein was precipitated using 5 volumes of ice-cold acetone and the precipitate for the permeate and retentate collected via centrifugation at 10,000×g for 20 min. The precipitate was resuspended in 2D-electrophoresis buffer containing 7M urea, 2M thiourea, 1.2% CHAPS, 0.4% ASB-14, 10 mM Tris HCl and 0.05% carrier ampholytes. Proteins were reduced using tributyl phosphine and alkylated with acrylamide monomers. Protein (100 μg) was loaded onto 24 cm pH 3-11 non linear IPG strips (GE Healthcare) and rehydrated overnight.

Figure 3:
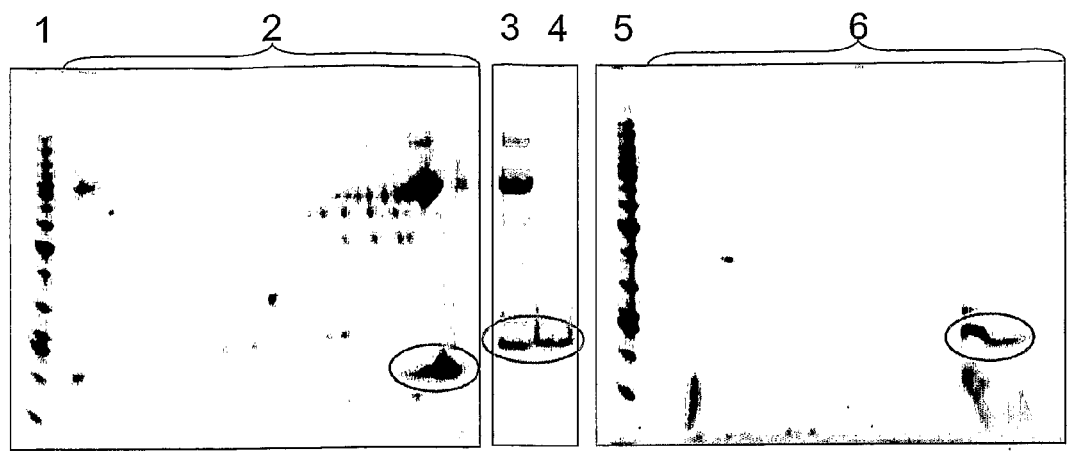
FIG. 3 shows electrophoretic separations comparing angiogenin-depleted retentate and the angiogenin-enriched permeate prepared by means of ultrafiltration through a 30 kDa membrane. Lane contents: 1, molecular weight standards; 2, 2D PAGE analysis of retentate; 3, 1D PAGE analysis of retentate; 4, 1D PAGE analysis of angiogenin-enriched permeate; 5, molecular weight standards; 6, 2D PAGE analysis of angiogenin-enriched permeate. The location of angiogenin is indicated by circles.

Isoelectric focussing used 100V for 2 h, 500V for 2 h, 1000V for 2 h, linearly increasing to 8000V over 4 h and finally 8000V for 8 h. IPG strips were equilibrated for 15 minutes in equilibration buffer containing 8M urea, 2% SDS prior to running in SDS PAGE using 50V for 1 h, followed by 150V for 12 h. Gels were fixed in acetic acid/methanol/water (1:3:6) and stained with Sypro Ruby (Invitrogen) overnight. Images were captured using ProXpress imaging system (Perkin Elmer) (FIG. 3). It was observed that the permeate was enriched in angiogenin as indicated by the bands contained within the circles in FIG. 3, and significantly lower in contaminating proteins.

Example 2b

Method of Obtaining a Product Enriched for Angiogenin from Skim Milk Using a Method According to the Third Aspect (Ultrafiltration)

The whey fraction containing growth factors was prepared in the same way as in Example 2a.

The whey fraction containing growth factors (2.5 g) was added to 95 g water and shaken at 250 rpm for 30 min to produce a 2.5% w/w solution. The solution (15 g) was placed into four Vivaspin 20 (GE Healthcare) centrifuge-driven ultrafiltration devices (10 kDa, 30 kDa, 50 kDa and 100 kDa). The tubes were centrifuged at 4,000×g for 10 min, which resulted in approximately 2 mL permeate passing through the membrane.

Figure 4:
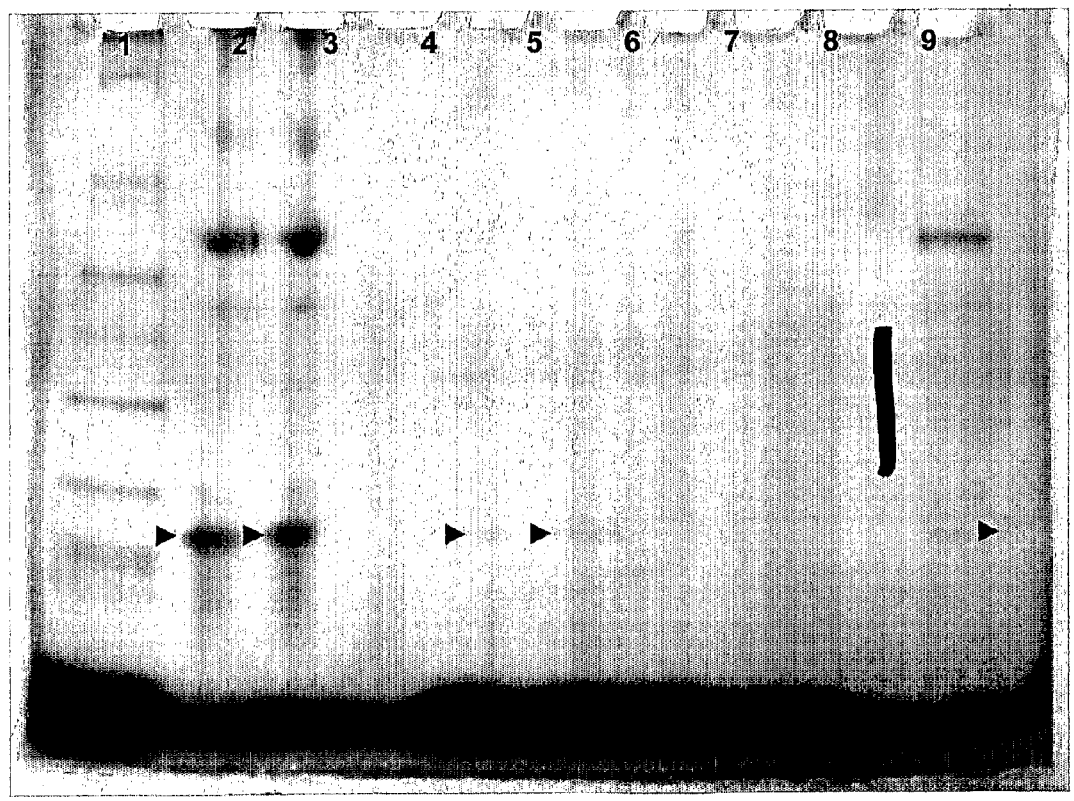
FIG. 4 shows a Tris-tricine PAGE gel showing separation of WGFE and fractions obtained by UF separation of WGFE or heat-induced precipitation of WGFE (Lane contents: 1, molecular weight standards; 2, heated WGFE; 3, heated WGFE; 4, empty; 5, 100 kDa permeate; 6, 50 kDa permeate; 7, 30 kDa permeate; 8, 10 kDa permeate; 9, empty; 10, unfractionated WGFE). The location of angiogenin is indicated (►).

The solution and ultrafiltration permeate were analysed by SDS PAGE. Each sample (100 μL) was mixed with 100 μL Tris-tricine sample buffer (NuSep, Frenchs Forest, Australia). Protein (10 μL) from each sample was applied to a Tris-tricine PAGE gel (16% acrylamide, NuSep), separated at 150V for 90 min and stained with Coomassie Blue (NuSep). Results are shown in FIG. 4. The 14 kDa peak present in unfractionated WGFE has previously been shown by mass spectroscopy to be angiogenin (PCT/AU2007/001719 'Process for the Preparation of Angiogenin' FIG. 2). Bands of an identical size to angiogenin were found to represent the major proteins present in the 50 kDa permeate and 100 kDa permeate. No angiogenin was present in the 10 kDa permeate and 30 kDa permeate. Angiogenin has previously been shown to penetrate through 30 kDa membranes so this result is surprising and probably anomalous.

Example 3

Method of Obtaining a Product Enriched for Angiogenin from Skim Milk According to the Fourth Aspect (Size Exclusion Chromatography)

The whey fraction containing growth factors was prepared in the same way as in Example 2a.

Figure 5:
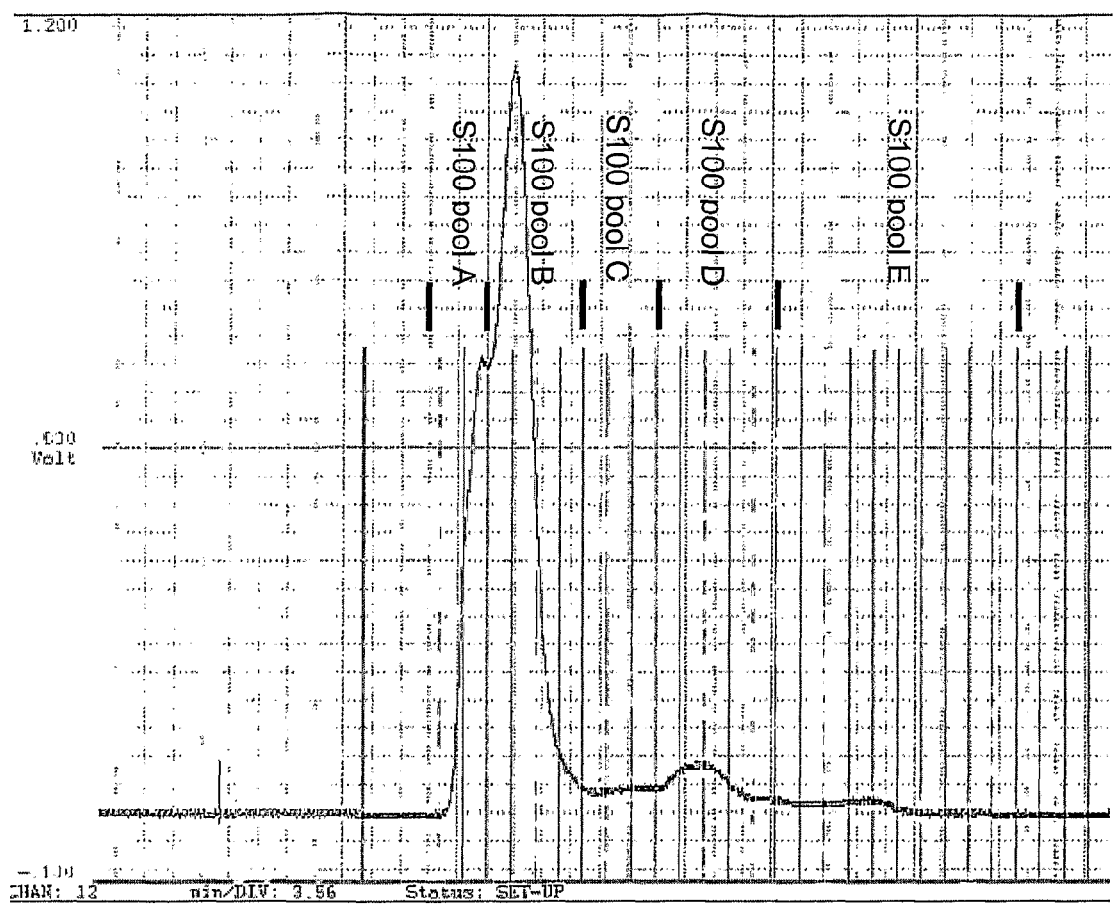
FIG. 5 shows Sephacryl S-100HR separation of WGFE to isolate angiogenin (—absorbance at 280 nm signal, —fraction collector signal, | pool start/end).
Figure 6:
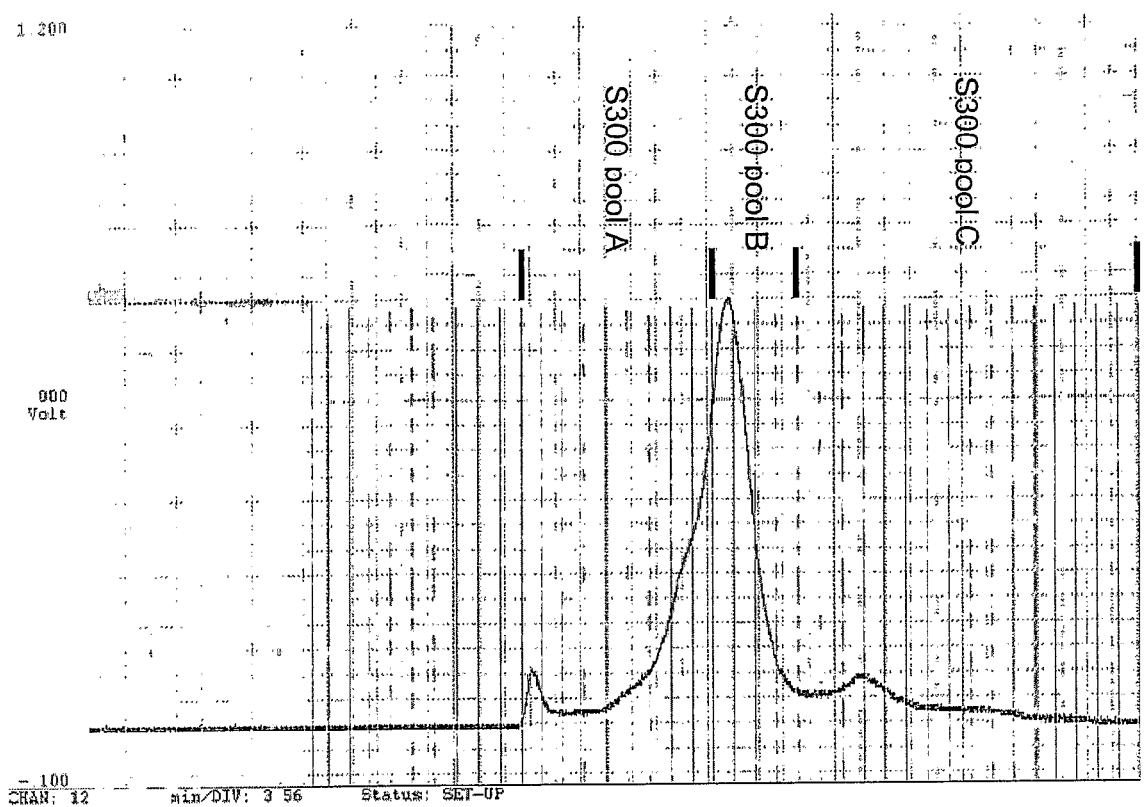
FIG. 6 shows Sephacryl S-300HR separation of WGFE to isolate angiogenin (—absorbance at 280 nm signal, —fraction collector signal, | pool start/end).
Figure 7:
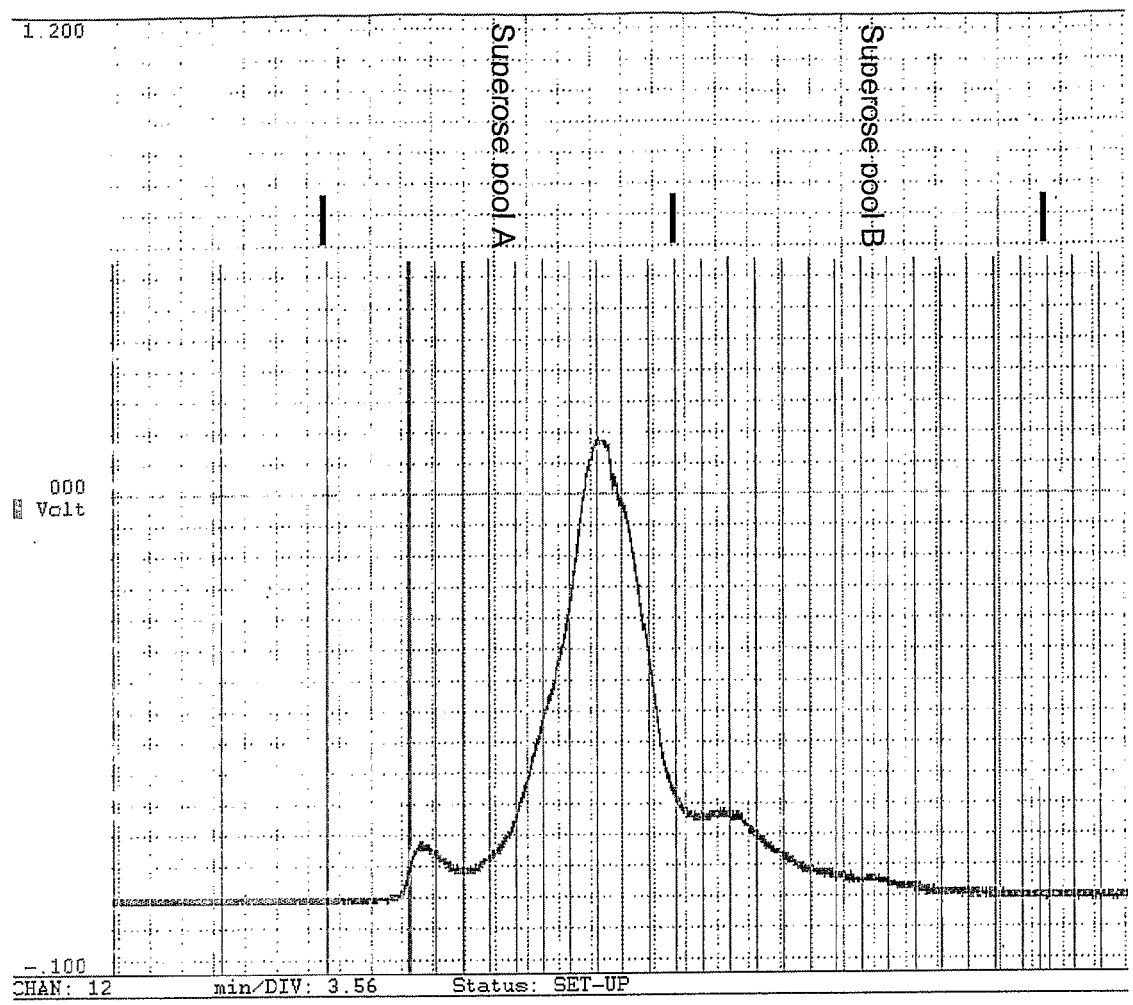
FIG. 7 shows Superose 12 separation of WGFE to isolate angiogenin (—absorbance at 280 nm signal, —fraction collector signal, | pool start/end).

Whey growth factors (5 g) were added to 45 g water and shaken at 250 rpm for 30 min to produce a 10% w/w solution. The WGFE solution was clarified by centrifugation (15,000×g for 6 min) and filtration (0.45 μm syringe-driven filter). Three size exclusion chromatography columns (Sephacryl S-100HR 26/60, Sephacryl S-300HR 26/60 and Superose 12 26 mmD×600 mL [all manufactured by GE Healthcare]) were equilibrated with 50 mM $Na_2HPO_4$ (pH7.0) at a flow rate of 3.5 mL/min. Protein solution was placed into a 50 mL Superloop (GE Healthcare) and then 5 mL WGFE solution was pumped onto each column. The WGFE solution was separated by pumping 50 mM $Na_2HPO_4$ (pH 7.0) through the column at a flow rate of 3.5 mL/min. The eluate was monitored at 280 nm (blue line) and 10 mL fractions were collected (grey line indicates the start of each fraction), as shown in FIGS. 5-7.

Figure 8:
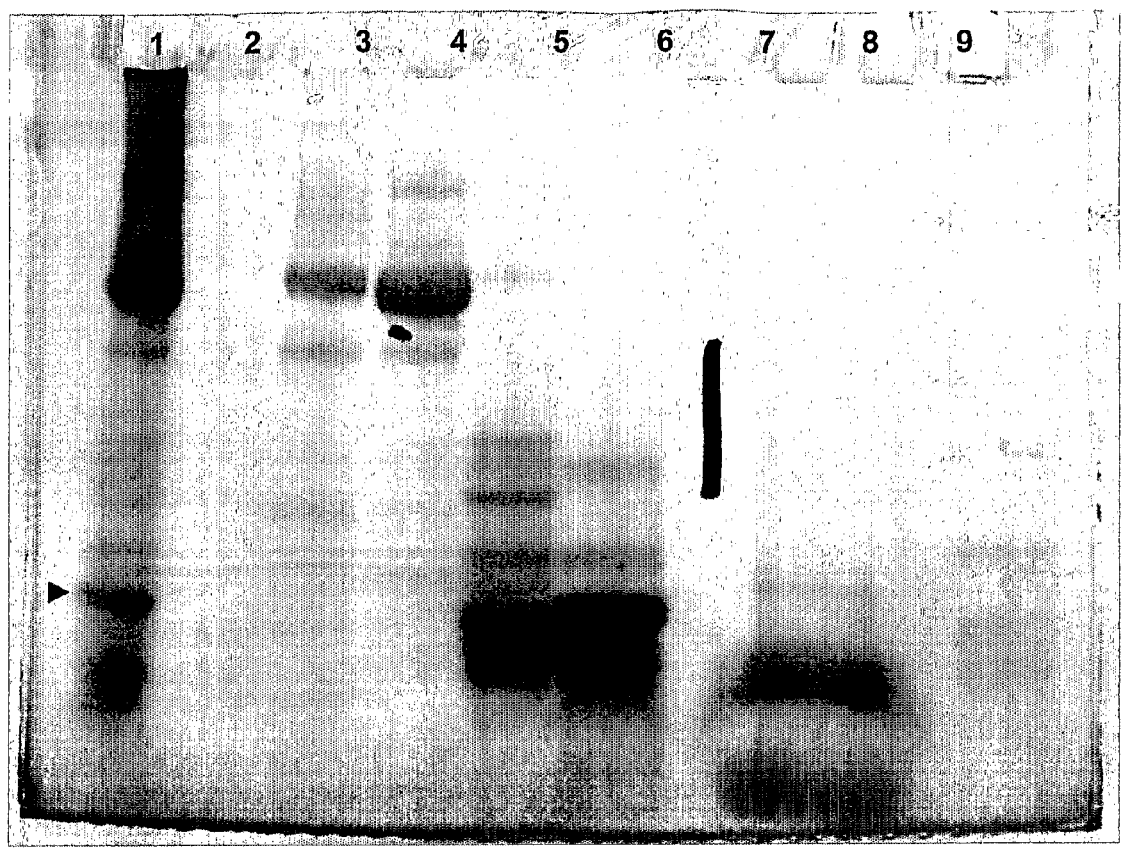
FIG. 8 is a Tris-tricine PAGE gel showing separation of WGFE and fractions obtained by SEC separation of WGFE (Lane contents: 1, unfractionated WGFE; 2, empty; 3, S-100HR pool A; 4, S-100HR pool B; 5, S-100HR pool C; 6, S-100HR pool D; 7, empty; 8, S-100HR pool E; 9, empty; 10, molecular weight standards). The location of angiogenin is indicated (▶).
Figure 9:
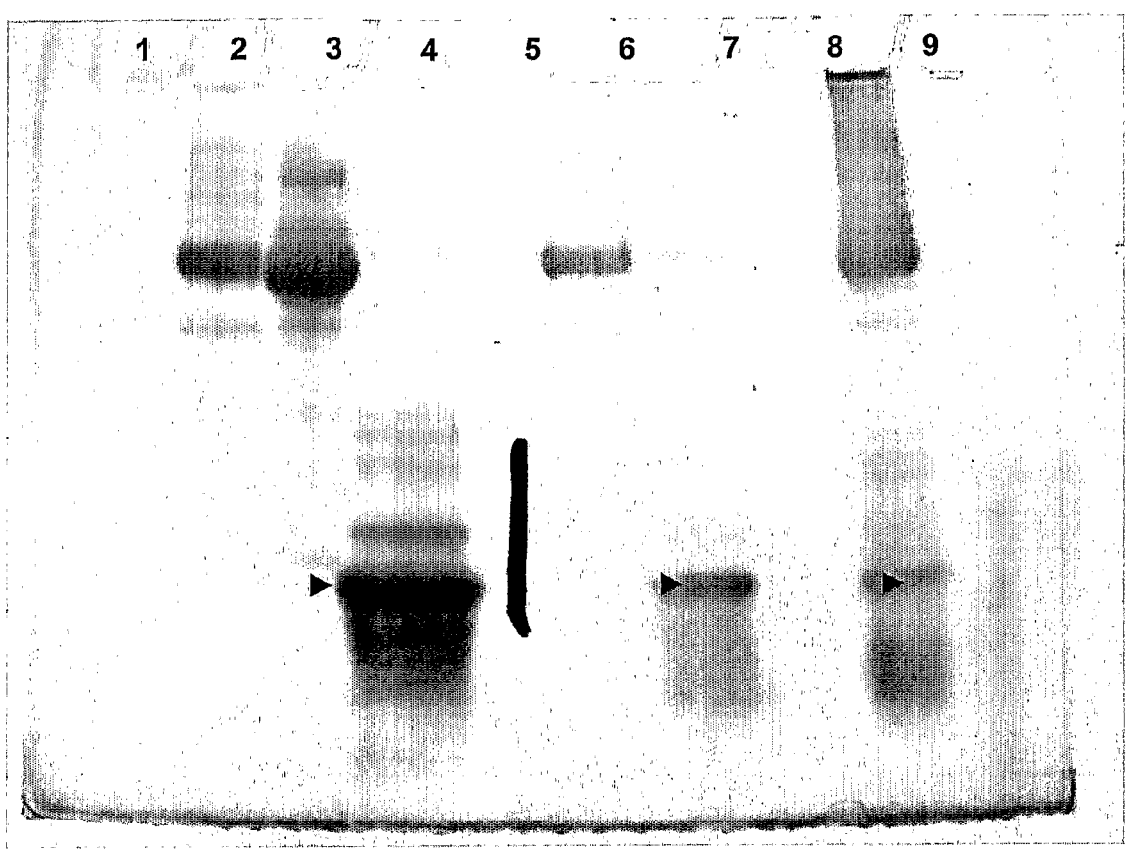
FIG. 9 is a Tris-tricine PAGE gel showing separation of WGFE and fractions obtained by SEC separation of WGFE (Lane contents: 1, empty; 2, S-300HR pool A; 2, S-300HR pool A; 3, S-300HR pool B; 4, S-300HR pool C; 5, empty; 6, Superose 12 pool A; 7, Superose 12 pool B; 8, empty; 9, unfractionated WGFE; 10, molecular weight standards). The location of angiogenin is indicated (▶).

Samples of like protein were pooled and the protein concentration estimated by BCA assay (Pierce, Rockford, Ill.). Samples with an insufficient protein concentration (<1 mg/mL) were concentrated in 5 kDa Vivaspin 20 centrifuge-driven ultrafiltration devices (GE Healthcare) until the protein concentration was greater than 1 mg/mL. Each sample (100 μL) was mixed with 100 μL Tris-tricine sample buffer (NuSep). Protein (0.02 mg) from each sample was applied to a Tris-tricine PAGE gel (16% acrylamide, NuSep), separated at 150V for 90 min and stained with Coomassie Blue (NuSep). The 14 kDa peak present in unfractionated WGFE has previously been shown by mass spectroscopy to be angiogenin (PCT/AU2007/001719 'Process for the Preparation of Angiogenin' FIG. 2). Peaks of an identical size to angiogenin were found in S-100HR pool D (FIG. 8), S-300HR pool C and Superose 12 pool B (FIG. 9).

Samples were also analysed by cation exchange HPLC. Samples (100 μL) were applied to a Mono S 5/50 GL column (GE Healthcare) that had been equilibrated with Buffer A (50 mM $NaH_2PO_4.H_2O$ and 5% [v/v] acetonitrile [pH7.0]). The sample was then eluted with increasing amounts of Buffer B (50 mM $NaH_2PO_4.H_2O$ and 2M NaCl [pH 7.0]) (Table 1). Eluate was monitored at 220 nm, 280 nm and 450 nm. Angiogenin has previously been shown by HPLC and subsequent mass spectroscopy to have a retention time of 5.8±0.1 min when analysed by this method and peaks with an identical retention time were assumed to be angiogenin and quantitated (Table 2).

TABLE 1

HPLC pump regime for cation exchange HPLC

| Time (min) | Flow (mL/min) | Buffer B (%) |
|---|---|---|
| 0.0 | 1 | 0 |
| 2.0 | 1 | 0 |
| 6.5 | 1 | 50 |
| 8.5 | 1 | 50 |
| 9.5 | 1 | 0 |
| 15.0 | 1 | 0 |

TABLE 2

Angiogenin purity as a percentage of protein determined by cation exchange HPLC

| Pool | Angiogenin purity (% protein) |
|---|---|
| Unfractionated WGFE | |
| WGFE | 5 |
| Sephacryl S-100HR | |
| A | 0 |
| B | 1 |
| C | 6 |
| D | 55 |
| E | 0 |
| Sephacryl S-300HR | |
| A | 1 |
| B | 0 |
| C | 40 |
| Superose 12 | |
| A | 1 |
| B | 27 |

Size exclusion chromatography has been shown as a suitable method for the isolation of angiogenin from a whey growth factor extract. Sephacryl S-100HR, Sephacryl S-300HR and Superose 12 were shown to be suitable, indicating that most SEC resins are suitable. Angiogenin enriched fractions containing greater than 55% angiogenin could be obtained by SEC. This degree of purity could be further improved by additional purification steps.

Example 4

Method of Obtaining a Product Enriched for Angiogenin from Skim Milk According to the Fifth Aspect (in-Solution Iso-Electric Focussing)

The method of in-solution isoelectric focussing has been broadly described previously but not in the context of angiogenin purification (see for example Michel P et al., 2003, *Electrophoresis;* 24, 3-11).

The applicants of the present invention have shown that angiogenin can now be extracted from a milk sample using methods disclosed herein.

The in-solution isoelectric focussing (ISIEF) method employed in this example is performed using the IsoelectrIQ$^2$ (Proteome Systems Limited, Australia). Fractionation is performed under native (aqueous) or denaturing conditions (including denaturants such as urea).

Prolyte (BD Diagnostics, Germany) or other electrolytes (acid or base) are also added for the creation of pH gradients. An example of a separation gradient is as follows:

Sample solubilisation solution (SSS): 7M urea, 2M thiourea and 1% 3-(4-heptyl)phenyl 3-hydroxypropyl dimethylammonio propane sulfonate (C7BzO).

Immediately prior to ISIEF separation, milk proteins were diluted in 10 volumes of SSS and 5 mM tributylphosphine and 5 mM ethylene diamine tetra-acetic acid was added. Using pH 3.0, 5.0, 6.5, 8.0 and 11.0 membranes (Proteome Systems Limited, Australia) sample separation chambers were created as follows, pH 3.0-5.0, pH 5.0-6.5, pH 6.5-8.0 and pH 8.0-11. Electrode solution (5 mL, supplied by vendor) was applied at the anode and cathode ends and 5 mL of milk protein resuspended in SSS added to the pH 5.0-6.5 chamber. SSS (5 mL) was added to the other chambers. Electrophoresis was performed at 14° C. with constant voltage of 100V for 2 h, a gradient to 1500V over 6 h, followed by constant voltage of 1500V for 8 h. The solution in each chamber was collected. The fraction enriched in angiogenin was collected from the cathodic end of the separation chambers (pH 8.0-11).

The presence of angiogenin was confirmed by two-dimensional SDS-PAGE, and staining with SYPRO Ruby according to manufacturer's instructions. For example, an aliquot equivalent to 40 µg of each protein faction was diluted to 128 µl with additional SSS. Ampholyte solution (0.6 µl of pH 3-11) and DeStreak solution (GE Healthcare) were added to each sample. Diluted samples were pipetted underneath 7 cm pH 3-11 NL IPG strips (GE Healthcare) and the IPG strips allowed to rehydrate overnight. Isoelectric focussing uses a protocol of 500V for 1 h, 1000V for 1 h, gradient to 5000V over 1 h and 5000V for 2 h. IPG strips were removed from isoelectric focussing apparatus and incubated for 15 minutes in equilibration buffer (EB; 6M urea, 2% sodium dodecyl sulphate, 20% glycerol, 50 mM Tris HCL (pH 8.8), 0.01% bromophenol blue) containing 100 mg dithiothreitol per 10 mL EB, followed by a second 15 minute incubation in EB containing 250 mg iodoacetamice per 10 mL EB. Reduced and alkylated IPG strips were loaded onto SDS PAGE gels (can be sourced from a provider; for example Invitrogen Novex precast Tris HCl gels) and the IPG strip sealed onto the gel by covering with hot running buffer (Tris base 3.03 g/L, glycine 14.4 g/L and SDS 1.0 g/L) containing 1.0% agarose, which was then allowed to cool. The gel was placed into the SDS PAGE apparatus and running buffer placed in the bottom and top wells of the apparatus. Electrophoresis was conducted at 200V for 1 hour. Following electrophoresis, proteins were fixed within the gel using fixing/destain solution (10% methanol and 7% acetic acid) prior to staining for at least 1 h with Sypro Ruby (Invitrogen). Gels were destained for at least 1 h in fixing/destain solution prior to imaging on a gel scanning system. Purity of fractions was determined by visual analysis of the images whereby the intensity and volume of each spot was assessed in a fraction.

Figure 10:
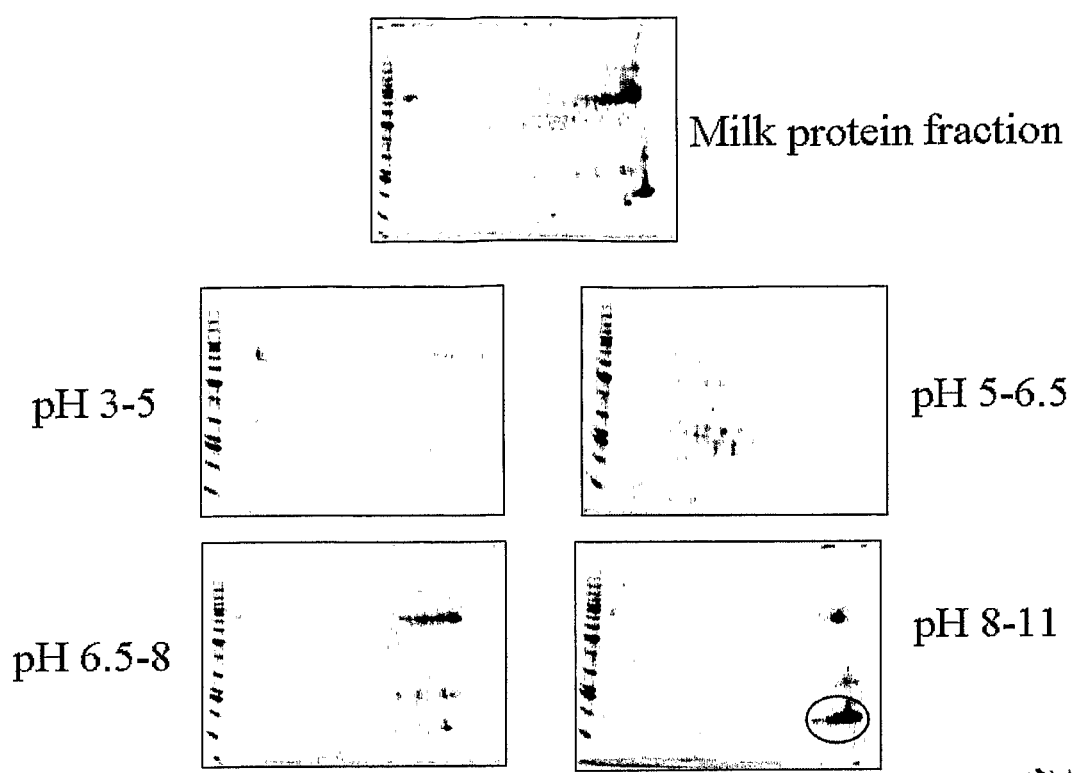
FIG. 10 shows 2-dimensional gel electrophoresis analysis of separation of proteins within in-solution isoelectric focussing experiments where a milk derived protein solution has been fractionated into pH 3-5, pH 6.5, pH 6.5-8 and pH 8-11 fractions. Approximately 80% of the protein within fraction pH 8-11 is identified as angiogenin.

FIG. 10 shows that the pH 8-11 fraction contains a low molecular weight (approximately 15 kDa) basic protein (approximate pI 10.0). This protein represents approximately 80% of the total protein within this fraction and the protein has been identified previously as angiogenin (PCT/AU2007/001719 'Process for the Preparation of Angiogenin' FIG. 2). FIG. 10 shows the resolution of basic proteins within the pH 8-11 fraction from the other proteins within the milk fraction.

Example 5

Effect of Heat on Methods of Obtaining a Product Enriched for Angiogenin

The whey fraction containing growth factors was prepared in the same way as in Example 2a.

The whey fraction containing growth factors (2.5 g) was added to 95 g water and shaken at 250 rpm for 30 min to produce a 2.5% w/w solution. The solution (10 g) was placed into a 15 mL glass test tube and placed into a water bath heated to 80° C. The temperature of the liquid inside the test tube was monitored with a temperature probe. The solution quickly reached 70° C. and was allowed to remain in the water bath for another minute (maximum temperature 75° C.). The test tube was removed from the hot water bath and cooled in a beaker of tap water.

The solution was transferred into a 10 mL centrifuge tube, centrifuged at 3,000×g for 7 min and the supernatant filtered (0.45 µm). The filtrate was analysed by SDS PAGE. Protein (0.001 mg WGFE, filtrate 0.025 mg less precipitation on heating) from each sample was applied to a Tris-tricine PAGE gel (16% acrylamide, NuSep), separated at 150V for 90 min and stained with Coomassie Blue (NuSep). The 14 kDa peak present in unfractionated WGFE has previously been shown by mass spectroscopy to be angiogenin (PCT/AU2007/001719 'Process for the Preparation of Angiogenin' FIG. 2). A band of an identical size to angiogenin was found to be present in the filtrate of the heated WGFE. Heating had enriched the angiogenin. In WGFE (lane 10) lactoperoxidase is the major protein, whereas heating WGFE leads to a sample where the angiogenin and lactoperoxidase are present in equal proportions (lanes 2 and 3), see FIG. 4. Persons skilled in the art would appreciate that a heating step prior to carrying out any of the methods of the first to fifth aspects and particularly the third to fifth aspects, should increase the purity of angiogenin in the enriched product.

It would be clear to a person skilled in the art that the angiogenin preparation methods described in each of the examples can be scaled up for commercial purposes and can be combined with additional purification steps either before or after carrying out the methods of any one of the first to fifth aspects in order to obtain angiogenin at a pharmaceutical grade purity.

The claims defining the invention are as follows:

1. A method of obtaining a product enriched for angiogenin from a milk sample, said method comprising:
   (a) contacting the milk sample with an anti-angiogenin antibody, such that angiogenin present in the milk sample interacts with the antibody to form an angiogenin-antibody complex;
   (b) separating the complex from the milk sample;
   (c) releasing angiogenin from the antibody in the complex; and
   (d) collecting the angiogenin from step (c) thereby obtaining a product enriched for angiogenin;
   in which the milk sample is heated to over 70° C. for at least one minute prior to step (a) to reduce the amount of lactoperoxidase and other proteins that denature at lower temperatures than angiogenin in the sample.

2. The method of claim 1 in which the antibody is immobilised to a support.

3. A method of obtaining a product enriched for angiogenin from a milk sample, said method comprising:
   (a) adding the milk sample to a support onto which is immobilised an antibody which interacts with angiogenin, wherein the angiogenin present in the milk sample interacts with the antibody on the support to form an angiogenin-antibody complex;
   (b) washing constituents present in the milk sample which do not interact with the antibody from the support to separate the complex from the milk sample;
   (c) releasing the angiogenin from the antibody in the complex; and
   (d) collecting the angiogenin from step (c) thereby obtaining a product enriched for angiogenin;

in which the milk sample is heated to over 70° C. for at least one minute prior to step (a) to reduce the amount of lactoperoxidase and other proteins that denature at lower temperatures than angiogenin in the sample.

4. A method of obtaining a product enriched for angiogenin from a milk sample, said method comprising:
   (a) adding a liquid phase milk sample to a second phase, said second phase enabling constituents of the milk sample to be separated based on the size of the constituents; and
   (b) collecting angiogenin which is separated from other constituents of the milk sample, thereby obtaining a product enriched for angiogenin;
   in which the milk sample is heated to over 70° C. for at least one minute prior to step (a) to reduce the amount of lactoperoxidase and other proteins that denature at lower temperatures than angiogenin in the sample and prior to step (a), the milk sample is not subject to rennetting or acid precipitation, or alternatively the milk sample is not whey or a whey fraction.

5. The method of claim 4 in which the second phase is a semi-permeable phase.

6. The method of claim 5 in which the milk sample is forced through the semi-permeable phase by means of force applied by a syringe, compressed gas, a pump, centrifugal force, or a combination thereof.

7. A method of obtaining a product enriched for angiogenin from a milk sample, said method comprising:
   (a) adding a liquid phase milk sample to a second phase, said second phase enabling constituents of the milk sample to be separated into fractions based on the size of the constituents;
   (b) identifying those fractions containing angiogenin and collecting said fractions to obtain a product enriched for angiogenin;
   in which the milk sample is heated to over 70° C. for at least one minute prior to step (a) to reduce the amount of lactoperoxidase and other proteins that denature at lower temperatures than angiogenin in the sample.

8. The method of claim 7 in which the second phase is a size exclusion resin.

9. The method of claim 7 in which the second phase separates proteins with a molecular weight of between about 10 and 20 kDa.

10. A method of obtaining a product enriched for angiogenin from a milk sample, said method comprising:
    (a) applying an electric field to a flowing aqueous milk sample in a direction transverse to the milk flow;
    (b) recovering fractions of the milk flow to which the electric field has been applied; and
    (c) identifying those fractions enriched for angiogenin and collecting said fractions, thereby obtaining a product enriched for angiogenin;
    in which the milk sample is heated to over 70° C. for at least one minute prior to step (a) to reduce the amount of lactoperoxidase and other proteins that denature at lower temperatures than angiogenin in the sample.

11. The method of claim 10 conducted under denaturing conditions.

12. The method of claim 10 in which the flow of aqueous milk is conducted in a buffer medium which provides a pH gradient.

13. The method of claim 1 in which the milk sample is selected from whole milk, skim milk, buttermilk, whey, a whey fraction and colostrum.

14. The method of claim 2 in which the milk sample is selected from whole milk, skim milk, buttermilk, whey, a whey fraction and colostrum.

15. The method of claim 3 in which the milk sample is selected from whole milk, skim milk, buttermilk, whey, a whey fraction and colostrum.

16. The method of claim 7 in which the milk sample is selected from whole milk, skim milk, buttermilk, whey, a whey fraction and colostrum.

17. The method of claim 10 in which the milk sample is selected from whole milk, skim milk, buttermilk, whey, a whey fraction and colostrum.

* * * * *